United States Patent
Zhang et al.

(10) Patent No.: US 8,521,268 B2
(45) Date of Patent: Aug. 27, 2013

(54) TECHNIQUES FOR DETERMINING CARDIAC CYCLE MORPHOLOGY

(75) Inventors: Xusheng Zhang, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 85 days.

(21) Appl. No.: 13/104,743

(22) Filed: May 10, 2011

(65) Prior Publication Data
US 2012/0289846 A1  Nov. 15, 2012

(51) Int. Cl.
*A61N 1/00* (2006.01)

(52) U.S. Cl.
USPC .............. 600/518; 600/509; 600/517

(58) Field of Classification Search
USPC .......................... 600/509, 517, 518
See application file for complete search history.

(56) References Cited

U.S. PATENT DOCUMENTS

| | | | |
|---|---|---|---|
| 5,779,645 A * | 7/1998 | Olson et al. | 600/518 |
| 6,393,316 B1 | 5/2002 | Gillberg et al. | |
| 6,728,572 B2 * | 4/2004 | Hsu et al. | 600/516 |
| 7,120,484 B2 | 10/2006 | Lu et al. | |

OTHER PUBLICATIONS

Toquero et al., "Morphology discrimination criterion wavelet improves rhythm discrimination in single-chamber implantable cardioverter-defibrillators: Spanish Register of morphology discrimination criterion wavelet (REMEDIO)," Europace (2009) 11, 727-733.

Theuns et al., "Evaluation of morphology discrimination for ventricular tachycardia disagnosis in implantable cardioverter-defibrillators," Heart Rhythm 2006;3:1332-1338.

* cited by examiner

*Primary Examiner* — Niketa Patel
*Assistant Examiner* — Lindsey G Hankins
(74) *Attorney, Agent, or Firm* — Michael C. Soldner

(57) ABSTRACT

A method includes storing an electrogram (EGM) template in a memory. The EGM template includes first and second alignment points at first and second peaks of the EGM template, respectively. The method further includes identifying first and second peaks of a cardiac cycle EGM acquired by a medical device and selecting one of the first and second peaks of the cardiac cycle EGM to align with one of the first and second alignment points based on an order in which the first and second peaks of the cardiac cycle EGM occur. Additionally, the method includes aligning the selected one of the first and second peaks with one of the first and second alignment points and determining an amount of similarity between the cardiac cycle EGM and the EGM template after alignment.

21 Claims, 15 Drawing Sheets

US 8,521,268 B2

TECHNIQUES FOR DETERMINING CARDIAC CYCLE MORPHOLOGY

TECHNICAL FIELD

The disclosure relates to techniques for determining cardiac cycle morphology, and more particularly, to determining cardiac cycle morphology using a template matching operation.

BACKGROUND

Implantable medical devices (IMDs), such as implantable cardioverter-defibrillators, may implement a variety of tachyarrhythmia detection and analysis algorithms. In some examples, IMDs may implement rate-based detection and analysis algorithms in order to detect and analyze tachyarrhythmias. IMDs may also implement template matching algorithms in order to determine the morphology of a detected tachyarrhythmia and to further classify the tachyarrhythmia. IMDs may provide therapy based on conclusions drawn from the use of these rate-based detection and template matching algorithms.

An IMD that implements a rate-based detection algorithm may monitor the length of intervals between sensed ventricular or atrial events, and detect a tachyarrhythmia when a predetermined number of those intervals are shorter than a programmed time interval. In some examples, IMDs may perform further analysis of tachyarrhythmias using rate information. For example, IMDs may characterize tachyarrhythmias based on the range of values in which the intervals fall, the stability of the intervals, and the average or median values of the intervals.

An IMD that implements a template matching algorithm may analyze the morphology of beats within a tachyarrhythmia by comparing the beats to a template that represents a particular beat morphology (e.g., a normal beat morphology). The IMD may determine whether each of the individual beats is similar or dissimilar to the template during the comparisons. After the comparisons, the IMD may identify the type of tachyarrhythmia based on how many of the beats included in the tachyarrhythmia are similar or dissimilar to the template beat morphology.

SUMMARY

Some IMDs may determine the morphology of a cardiac cycle by comparing the cardiac cycle to a template of a known morphology. In some examples, the template to which the cardiac cycle is compared may include a single alignment point at the largest peak in the template. During a typical comparison between the cardiac cycle and the template, the IMD may align the largest peak of the cardiac cycle with the single alignment point of the template. The IMD may determine the amount of similarity between the aligned cardiac cycle and the template, and then determine the morphology of the cardiac cycle based on the amount of similarity.

Aligning a cardiac cycle with a template having only a single alignment point at the largest peak may be satisfactory in scenarios when the template and cardiac cycle morphology include only single prominent peaks, since the single prominent peaks of the template and cardiac cycle may be the defining features of the template and cardiac cycle and may match well together. However, in some scenarios, the template and cardiac cycle may each include multiple prominent peaks of similar magnitude such that none of the multiple prominent peaks alone form distinct morphological features in either the template or the cardiac cycle. In these scenarios, the selection of one of the multiple prominent peaks of the cardiac cycle for alignment with one of the multiple prominent peaks of the template based on the magnitude of the peaks alone may not provide for reliable alignment since, based on magnitude alone, the peaks of the cardiac cycle or the template may not be morphologically distinct. Therefore, when a template and a cardiac cycle include multiple prominent peaks, matching of the cardiac cycle to a template using only a single alignment point may be unreliable in terms of correctly identifying the similarity between the cardiac cycle and the template.

An IMD, or other device, of the present disclosure may include a template that may be used during a matching operation to determine a morphology of a cardiac cycle. The template may have the morphology of a normal cardiac cycle, e.g., a cardiac cycle of a normal heartbeat for the patient, or an averaged cardiac cycle over a plurality of normal cardiac cycles. In some examples, a clinician may generate or select the template and upload the generated template to the IMD. In other examples, the device may generate the template and periodically update the template. The IMD may characterize a generated template as a single-peak template or a dual-peak template, depending on the morphology of the template. In some examples, the IMD may characterize a generated template as a single-peak template when the template includes only a single prominent peak. The single prominent peak of the single-peak template may serve as an alignment point to which an acquired cardiac cycle may be aligned. In other examples, the IMD may characterize a generated template as a dual-peak template when the template includes two or more prominent peaks having the same polarity. The IMD may select two of the prominent peaks of the dual-peak template to serve as alignment points to which features of an acquired cardiac cycle may be aligned.

In some examples, the IMD, or other device, of the present disclosure may include a dual-peak template, either generated by a clinician or generated by the IMD. In these examples, the IMD may determine a morphology of a cardiac cycle by comparing the cardiac cycle to the dual-peak template that includes two alignment points, the alignment points located at peaks of the dual-peak template. The IMD of the present disclosure may acquire a cardiac cycle, characterize the cardiac cycle as one of a single-peak cycle or a dual-peak cycle, then align the characterized cardiac cycle with the dual-peak template based on the characterization of the cardiac cycle and other morphological features of the cardiac cycle. In some examples, the dual-peak cycle may include two prominent peaks of the same polarity, while the single-peak cycle may include a first peak, but not a second prominent peak having the same polarity as the first peak.

If the IMD characterizes a cardiac cycle as a single peak cycle, the IMD may align the largest peak of the single-peak cycle with the largest peak of the dual-peak template. If the IMD characterizes the cardiac cycle as a dual-peak cycle, the IMD may align the dual-peak cycle to the dual-peak template in one of two ways. In one example, when the order, by magnitude, of the peaks in the dual-peak cycle is the same as the order, by magnitude, of the peaks in the dual-peak template, the IMD may align the largest peaks of the dual-peak cycle and the dual-peak template. In another example, when the order, by magnitude, of the peaks in the dual-peak cycle is different than the order, by magnitude, of the peaks in the dual-peak template, the IMD may align the leftmost peaks of the dual-peak cycle and the dual-peak template. Subsequent to alignment, the IMD may determine an amount of similarity between the cardiac cycle and the dual-peak template to determine the morphology of the cardiac cycle.

The morphological characterization of an acquired cardiac cycle as either a single-peak cycle or a dual-peak cycle, followed by the alignment of the cardiac cycle relative to the dual-peak template based on the order of the peaks of the cardiac cycle, may provide for reliable template matching of cardiac cycles including multiple prominent peaks. In one sense, characterization of a cardiac cycle as either a single-peak cycle or a dual-peak cycle identifies those cardiac cycles, e.g., dual-peak cycles, that may include multiple prominent peaks, and therefore may cause problems during alignment and matching. In a second sense, those cycles having multiple prominent peaks, e.g., dual-peak cycles, are subjected to further analysis based on the order of the peaks (by magnitude) in the cardiac cycle relative to the order of the peaks (by magnitude) in the template. This further analysis based on peak order of the cardiac cycle relative to peak order of the dual-peak template may increase reliability of the alignment operation by providing for more reliable alignment between similar morphologies in the cardiac cycle and the template, assuming such similar morphologies actually exist. More reliable alignment may result in more accurate matching scores, and therefore more reliable identification of cardiac cycle morphology than may be obtained using other alignment techniques such as those techniques using only a single alignment point in a template.

In one example according to the present disclosure, a method comprises storing an electrogram (EGM) template in a memory. The EGM template includes first and second alignment points at first and second peaks of the EGM template, respectively. The method further comprises identifying first and second peaks of a cardiac cycle EGM acquired by a medical device and selecting one of the first and second peaks of the cardiac cycle EGM to align with one of the first and second alignment points based on an order in which the first and second peaks of the cardiac cycle EGM occur. Additionally, the method comprises aligning the selected one of the first and second peaks with one of the first and second alignment points and determining an amount of similarity between the cardiac cycle EGM and the EGM template after alignment.

In another example according to the present disclosure, a device comprises a memory and a processing module. The processing module stores an EGM template in the memory. The EGM template includes first and second alignment points at first and second peaks of the EGM template, respectively. The processing module acquires a cardiac cycle EGM, identifies first and second peaks of the cardiac cycle EGM, and selects one of the first and second peaks of the cardiac cycle EGM to align with one of the first and second alignment points based on an order in which the first and second peaks of the cardiac cycle EGM occur. The processing module aligns the selected one of the first and second peaks with one of the first and second alignment points and determines an amount of similarity between the cardiac cycle EGM and the EGM template after alignment.

In another example according to the present disclosure, a method comprises storing an EGM template in a memory of an implantable medical device (IMD). The EGM template includes first and second alignment points at first and second peaks of the EGM template, respectively. The method further comprises detecting a tachyarrhythmia based on N cardiac cycles using the IMD. N is an integer greater than 1. Additionally, the method comprises, for each of the N cardiac cycles, identifying first and second peaks of the cardiac cycle, selecting one of the first and second peaks of the cardiac cycle to align with one of the first and second alignment points based on an order in which the first and second peaks of the cardiac cycle occur. The method further comprises, for each of the N cardiac cycles, aligning the selected one of the first and second peaks with one of the first and second alignment points, and detecting one of a match or a mismatch between the cardiac cycle and the EGM template based on the amount of similarity between the cardiac cycle and the EGM template after alignment. Additionally, the method comprises identifying the rhythm of the N cardiac cycles based on a number of detected matches and detected mismatches.

The details of one or more examples are set forth in the accompanying drawings and the description below. Other features, objects, and advantages will be apparent from the description and drawings, and from the claims.

DETAILED DESCRIPTION

Figure 1:
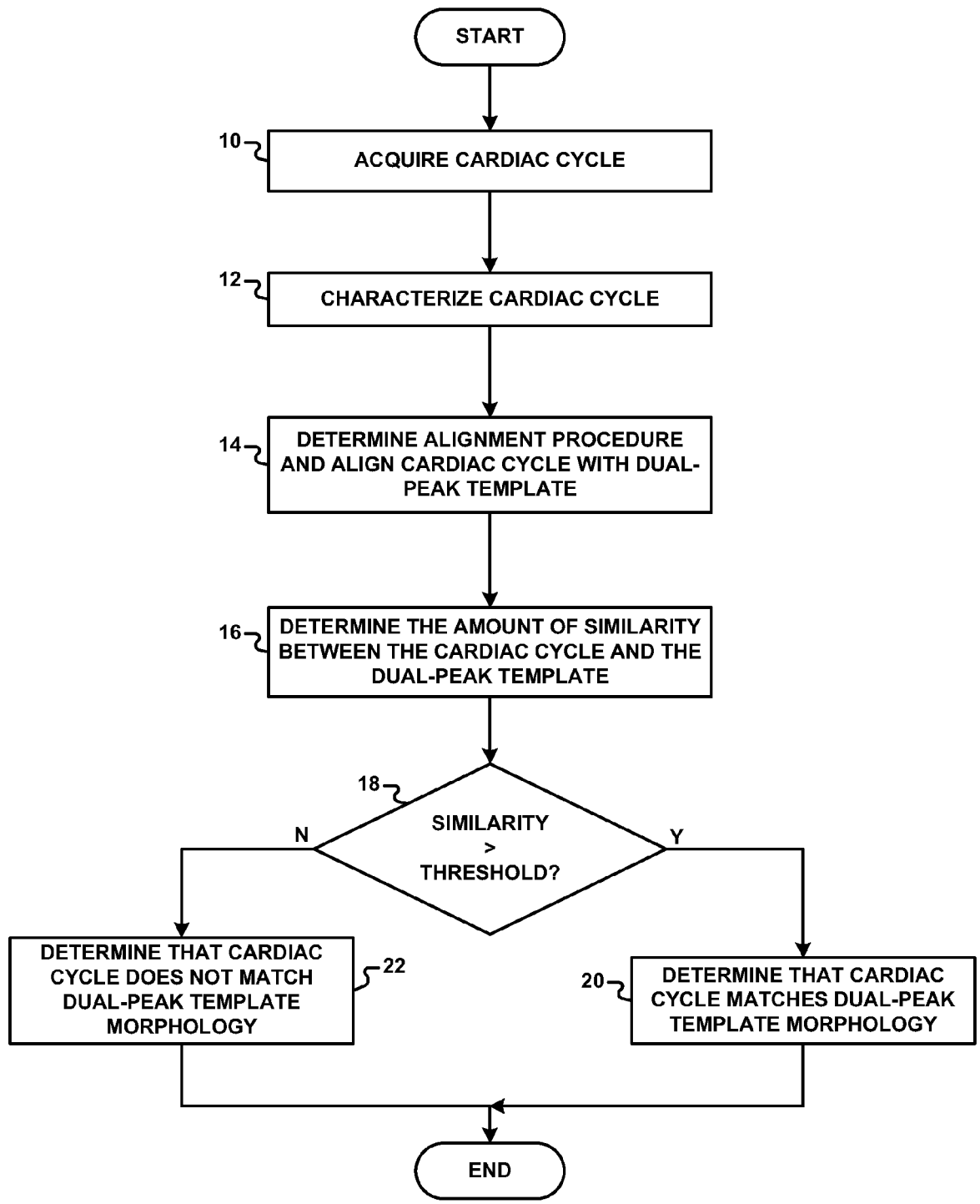
FIG. 1 shows an example method for determining the morphology of a single cardiac cycle.

An IMD, or other device, according to the present disclosure may determine the morphology of a cardiac cycle electrogram (EGM) (hereinafter "cardiac cycle") by determining the amount of morphological similarity between the cardiac cycle and a template having a known morphology. The template may have the morphology of a normal cardiac cycle, e.g., a cardiac cycle of a normal heartbeat for a patient in which the IMD is implanted, or an averaged cardiac cycle based on a plurality of normal cardiac cycles. In some examples, a clinician may generate the template based on data received from the IMD, and then subsequently upload the generated template to the IMD. In other examples, the IMD may automatically generate the template and periodically update the template during operation.

The morphology of the generated template may vary from patient to patient, and may vary within a single patient from update to update. In some examples, the generated template may include only a single prominent peak. In other examples, the template may include multiple prominent peaks of the same polarity. After a template is generated and loaded into the IMD, e.g., by the clinician, or automatically by the IMD, the IMD of the present disclosure may characterize the template as either a single-peak template or a dual-peak template, based on a morphology of the template. The IMD may characterize the morphology of the template, for example, based on a number of detected peaks in the template, a magnitude of the detected peaks in the template, the polarity of the detected peaks, and the location of the detected peaks.

In some examples, the IMD may characterize a generated template as a single-peak template when the template includes only a single prominent peak. The single prominent peak of the single-peak template may serve as an alignment point to which an acquired cardiac cycle may be aligned prior to determining the amount of morphological similarity between the cardiac cycle and the single-peak template. In other examples, the IMD may characterize a generated template as a dual-peak template when the template includes two or more prominent peaks having the same polarity. The IMD may select two of the prominent peaks of the dual-peak template to serve as alignment points to which features of an acquired cardiac cycle may be aligned.

Generally, the IMD may determine how to align an acquired cardiac cycle with a template based on the morphology of the template and a morphology of the acquired cardiac cycle. In examples where the IMD has characterized the template as a single-peak template, the IMD may identify the largest peak of the cardiac cycle having the same polarity as the single alignment point, and subsequently align the acquired cardiac cycle with the single-peak template by aligning the largest peak of the cardiac cycle with the single alignment point of the single-peak template. When the template included in the IMD is characterized as a dual-peak template, the IMD may determine how to align the template with an acquired cardiac cycle according to the techniques of the present disclosure which are described hereinafter in further detail.

An EGM of a cardiac cycle may include digitized data (i.e., raw data) of cardiac electrical activity that occurs from the beginning of one heartbeat to the beginning of the next heartbeat, as sensed by electrodes of the IMD. Cardiac electrical activity in a typical cardiac cycle may include a P wave, a QRS complex, a T wave, and a U wave. During a cardiac cycle, cardiac electrical activity may exhibit a baseline voltage, which may be referred to as an isoelectric line, which may be measured between a T wave of a recent cardiac cycle and a P wave of the following cardiac cycle. Morphology of a cardiac cycle may refer to the general shape characteristics of the cardiac cycle, including, but not limited to, peak values of the cardiac cycle, slope values of the cardiac cycle, a width of the cardiac cycle, and other quantifiable features of the cardiac cycle.

Before determining the amount of morphological similarity between an acquired cardiac cycle and a dual-peak template, the IMD may first determine how to align the cardiac cycle with the dual-peak template based on the morphology of the cardiac cycle, then align the cardiac cycle with the dual-peak template based on the determination. The IMD may then quantify the amount of similarity between the cardiac cycle and the dual-peak template. The IMD may determine whether the cardiac cycle morphology matches the template morphology based on the quantified amount of similarity. For example, the IMD may determine that the cardiac cycle has the same morphology as the dual-peak template when the amount of similarity between the cardiac cycle and the dual-peak template is greater than a threshold amount. Alternatively, the IMD may determine that the cardiac cycle has a different morphology than the dual-peak template when the amount of similarity is less than the threshold amount. In examples where the dual-peak template has a normal beat morphology, the IMD may determine that the cardiac cycle is a normal cardiac cycle when the amount of similarity between the cardiac cycle and the dual-peak template is greater than a threshold amount. Alternatively, in these examples, the IMD may determine that the cardiac cycle may not have a normal beat morphology when the amount of similarity between the cardiac cycle and the dual-peak template is less than the threshold amount.

In some examples, the IMD may acquire a plurality of cardiac cycles, determine the morphology of each of the plurality of cardiac cycles by comparing each of the cardiac cycles to the dual-peak template, and identify the rhythm indicated by the cardiac cycles based on the morphology of each of the cardiac cycles. In one example, the IMD may detect a tachyarrhythmia of the patient, e.g., using a rate-based detection algorithm, and subsequently further identify the rhythm based on the morphology of the cardiac cycles included in the tachyarrhythmia. For example, the IMD may determine that the tachyarrhythmia is supraventricular in origin, e.g., a supraventricular tachycardia (SVT), when a threshold number of the cardiac cycles included in the tachyarrhythmia are found to be similar to the dual-peak template that has a normal cardiac cycle morphology. In other examples, the IMD may determine that the tachyarrhythmia is a ventricular tachycardia (VT) or ventricular fibrillation (VF) when less than a threshold number of the cardiac cycles included in the tachyarrhythmia are determined to be similar to the dual-peak template having the normal cardiac cycle morphology.

As described above, the IMD may determine how to align the cardiac cycle with the dual-peak template based on the morphology of the cardiac cycle. The IMD may characterize the cardiac cycle morphology in one of at least two ways. For example, the IMD may characterize the cardiac cycle as either a "single-peak cycle" or a "dual-peak cycle." The IMD may then determine how to align the cardiac cycle with the dual-peak template based on the characterization of the cardiac cycle. The IMD may characterize the cardiac cycle based on morphological features of the cardiac cycle, such as a number of identified peaks of the cardiac cycle, an order of the peaks, and a polarity of the peaks, for example.

A "peak," as described herein, may refer to a local or global maximum value within an acquired cardiac cycle. A global maximum value of a cardiac cycle may be the maximum value within the cardiac cycle relative to the baseline of the cardiac cycle, e.g., either the largest positive value within the cardiac cycle or the largest negative value within the cardiac cycle. Typically, the global maximum value of a cardiac cycle is at a region of the cardiac cycle having a zero slope. A local maximum value within the cardiac cycle may refer to a value at a zero-slope region of the cardiac cycle that is less than the global maximum value in the cardiac cycle. Referring to FIG.

12A, a global maximum value of cardiac cycle 172 is indicated at 171, while local maximum values are indicated at 1, 2, and 3. The global maximum value may be the largest peak of the cardiac cycle 172, while one of the local maximum values may be the second largest peak of the cardiac cycle 172.

Upon generation of a template, the IMD may characterize the generated template as either a single-peak template or a dual-peak template based on the morphology of the template. For example, the IMD may characterize a generated template as either a single-peak template or a dual-peak template based on a number of detected peaks in the template, a magnitude of the detected peaks in the template, the polarity of the detected peaks, and the location of the detected peaks within the template.

Generally, the IMD may characterize a generated template as a dual-peak template when the IMD identifies two peaks having the same polarity (e.g., voltage polarity) within the template, although the IMD may require that the generated template includes some further features, in other examples, to be characterized as a dual-peak template. The IMD may characterize a template as a dual-peak template according to the following approach. First, the IMD may identify the largest peak within the template. Then the IMD may determine whether a second peak, having the same polarity as the largest peak, exists within the template. For example, the IMD may determine that a second peak exists when a second peak is identified that has the same polarity as the largest peak, and also has a magnitude that is greater than a threshold magnitude relative to the largest peak, e.g., greater than half the magnitude of the largest peak. The IMD may then designate the largest peak and the second peak as alignment points of the dual-peak template.

The constraint on the magnitude of the second peak, e.g., that the second peak has a magnitude that is greater than a threshold magnitude, may assure that the peak of the template identified as the second peak is truly a distinct peak in relation to the largest peak, and not a morphology of the template that may be indicative of drift or another physiologically insignificant phenomenon. In some examples, after identifying the second peak, the IMD may require that the largest peak and the second peak be located a predetermined distance apart from one another for the template to qualify as a dual-peak template. For example, the predetermined distance may be a predetermined number of sample points (e.g., 2 sample points). Such a constraint may assure that the second peak of the template is truly a distinct peak in relation to the largest peak of the template, and not an artifact (e.g., noise spike or other physiologically insignificant signal) of the template that is included on a slope on either side of the largest peak.

When the template may not be classified as a dual-peak template, e.g., if the template does not include two peaks of the same polarity, the IMD may characterize the template as a single-peak template. Generally, a single-peak template may not include a second prominent peak (e.g., of a threshold magnitude) having the same polarity as the largest peak. The IMD may designate the single prominent peak of the single-peak template as the single alignment point of the single-peak template.

The IMD may align a single-peak cycle with the single-peak template in a similar manner as the IMD aligns a dual-peak cycle with the single-peak template. Prior to aligning either a single-peak cycle or a dual-peak cycle with the single-peak template, the IMD may determine the largest peak of the cardiac cycle (e.g., either single-peak or dual-peak) having the same polarity as the single alignment point of the single-peak template. Subsequently, the IMD may align the acquired cardiac cycle with the single-peak template by aligning the largest peak of the cardiac cycle with the single alignment point of the single-peak template. When the template included in the IMD is a dual-peak template, the IMD may determine how to align the template with an acquired cardiac cycle according to the techniques of the present disclosure, which are described in greater detail hereinafter.

As described above, the dual-peak template of the present disclosure may include two or more peaks. Two peaks of the dual-peak template may be used as alignment points during alignment of the cardiac cycle and the dual-peak template. The two peaks of the dual-peak template used as alignment points may have the same polarity. The larger of the two peaks that may be used for alignment may be referred to as the "larger template peak." The smaller of the two peaks that may be used for alignment may be referred to as the "smaller template peak." The larger template peak may be the global maximum value of the dual-peak template, while the smaller template peak may be one of the local maximum values of the dual-peak template having the same polarity as the larger template peak. The dual-peak template may be a digitized version of a cardiac cycle, e.g., a normal cardiac cycle in some examples, or an averaged cardiac cycle over a certain number of normal cardiac cycles. In addition to storing the dual-peak template in memory, the IMD may store parameters of the dual-peak template that describe the morphology of the template. For example, parameters may include the location of the two peaks (i.e., the sample numbers within the cardiac cycle, such as the $10^{th}$ and $33^{rd}$ of 50 samples), the magnitudes of the two peaks (e.g., in milli-volts (mV)), and the polarities of the two peaks (i.e., whether positive or negative). Although the IMD of the present disclosure is described as including a dual-peak template hereinafter, as described above, the IMD may include other templates (e.g., a single-peak template) to which a cardiac cycle may be compared. Furthermore, as described above, the IMD may periodically update the stored template, which may result in either a single-peak template or a dual-peak template being stored in memory.

The IMD may characterize a cardiac cycle as either a single-peak cycle or a dual-peak cycle, and then perform the alignment operation with the dual-peak template based on the characterization. Generally, the IMD may characterize a cardiac cycle as a dual-peak cycle when the IMD identifies two peaks having the same polarity (e.g., voltage polarity) as the template peaks within the cardiac cycle, although the IMD may require that the cardiac cycle includes some further features, in other examples, to be characterized as a dual-peak cycle. When the cardiac cycle may not be classified as a dual-peak cycle, e.g., if the cardiac cycle does not include two peaks of the same polarity as the template peaks, the IMD may characterize the cardiac cycle as a single-peak cycle. Generally, a single-peak cycle may not include a second prominent peak (e.g., of a threshold magnitude) having the same polarity as the largest peak. Characterization of cardiac cycles is explained in greater detail with respect to FIG. 5.

When the IMD has characterized the cardiac cycle as a single-peak cycle, the IMD may align the single peak of the cardiac cycle with the larger template peak during the alignment operation. When the IMD has characterized the cardiac cycle as a dual-peak cycle, the IMD may align the dual-peak cycle and the dual-peak template in one of at least two ways. In one example, the IMD may align the leftmost peaks of the cardiac cycle and the dual-peak template. In another example, the IMD may align the largest peak of the dual-peak cycle with the larger template peak. Details regarding alignment between a cardiac cycle and the dual-peak template are described in greater detail with respect to FIGS. 6-7.

FIG. 1 shows an example method for determining the morphology of a single cardiac cycle. The method of FIG. 1 may be implemented by an IMD, or any computing device that communicates with the IMD, such as a programmer of the IMD, or a remote server. An IMD may perform the method of FIG. 1 for each of a plurality of cardiac cycles in order to identify a rhythm (e.g., SVT, VT, VF) indicated by the plurality of cardiac cycles, as described with respect to FIG. 15, for example.

Figure 2:
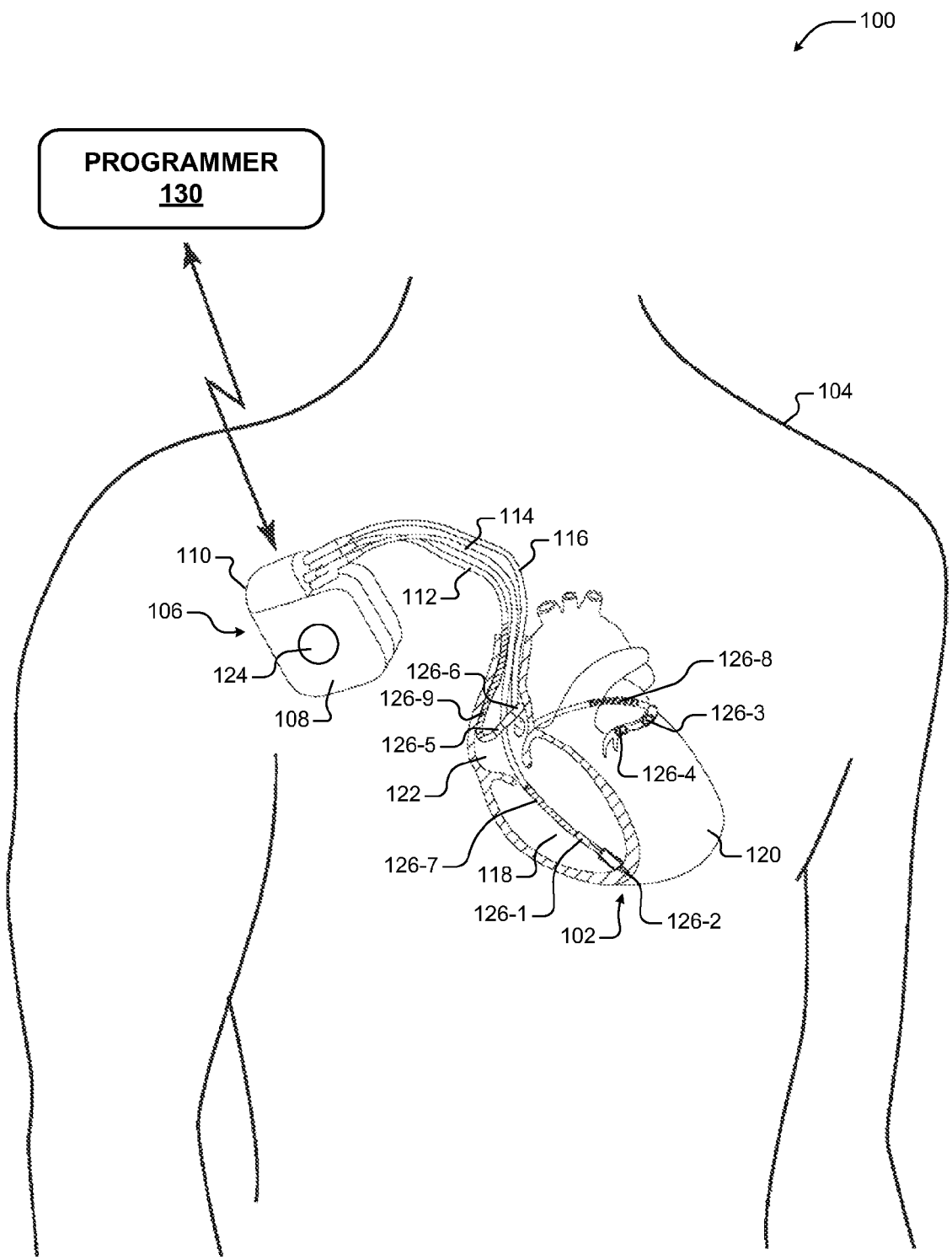
FIG. 2 shows an example system including an implantable medical device (IMD) that may be used to diagnose conditions of and provide therapy to a heart of a patient.
Figure 3:
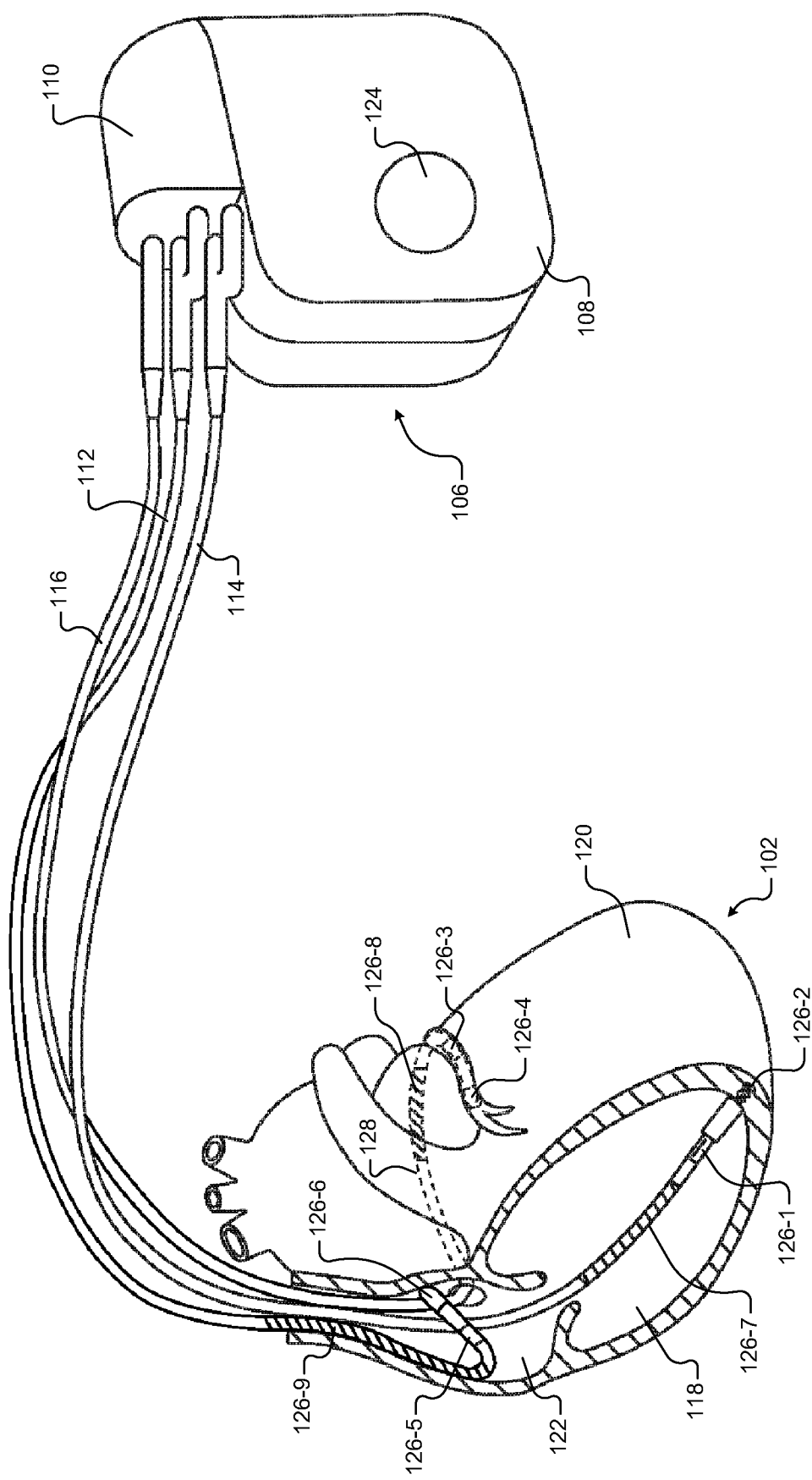
FIG. 3 shows a detailed view of the IMD of FIG. 2.
Figure 4:
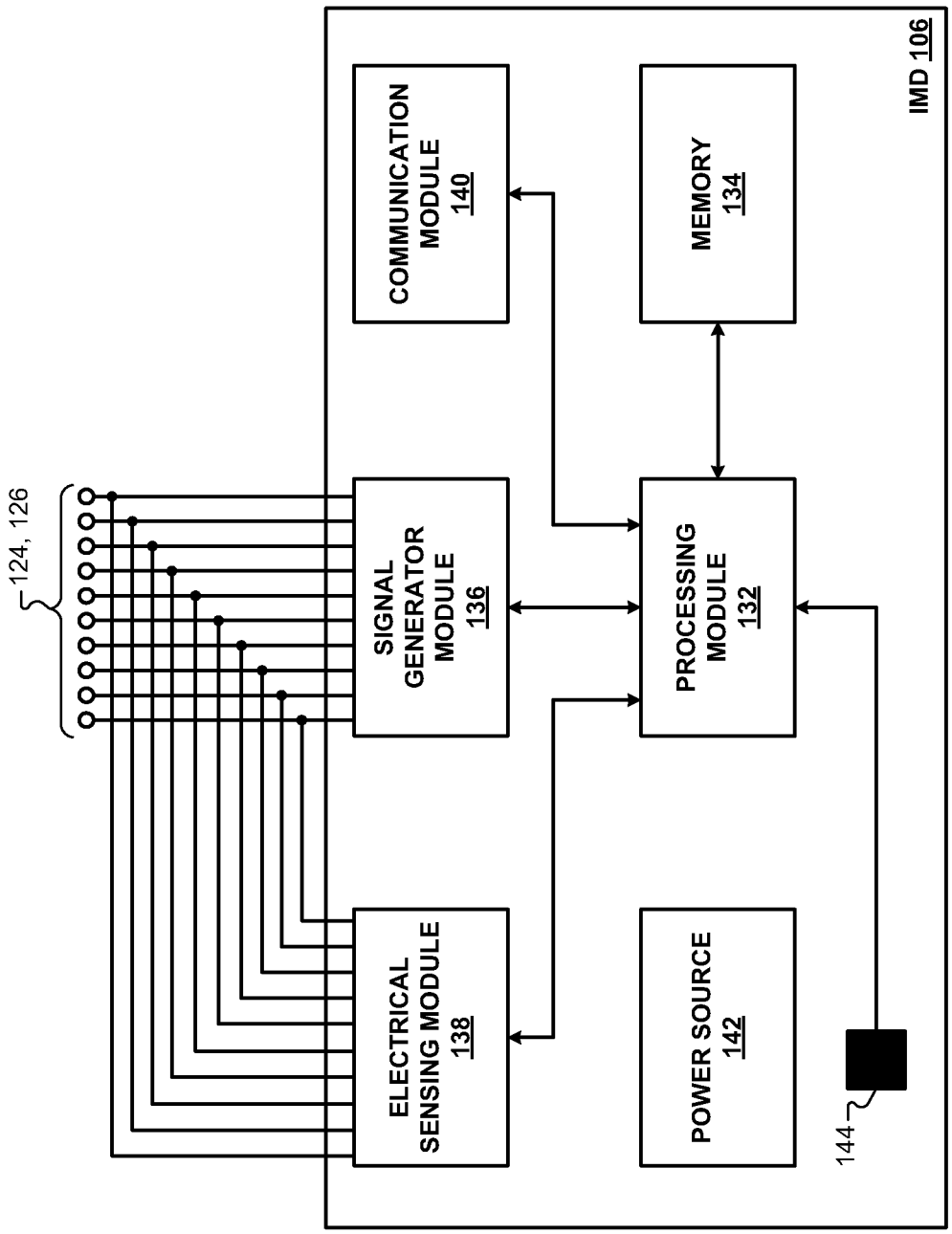
FIG. 4 shows a functional block diagram of an example IMD.
Figure 9:
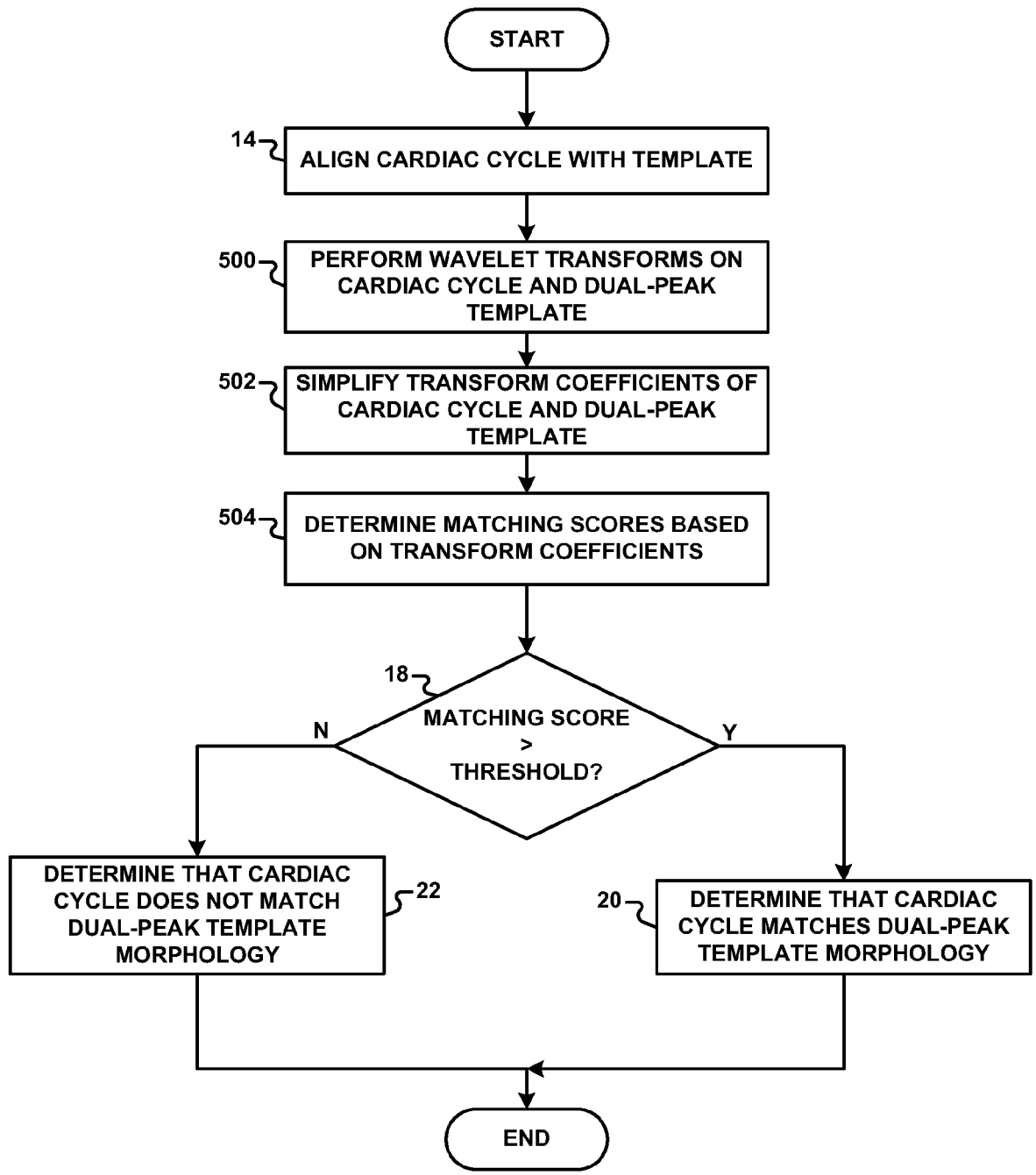
FIG. 9 shows a method for determining a morphology of a cardiac cycle by comparing a transform of the cardiac cycle and a transform of the dual-peak template.
Figure 10:
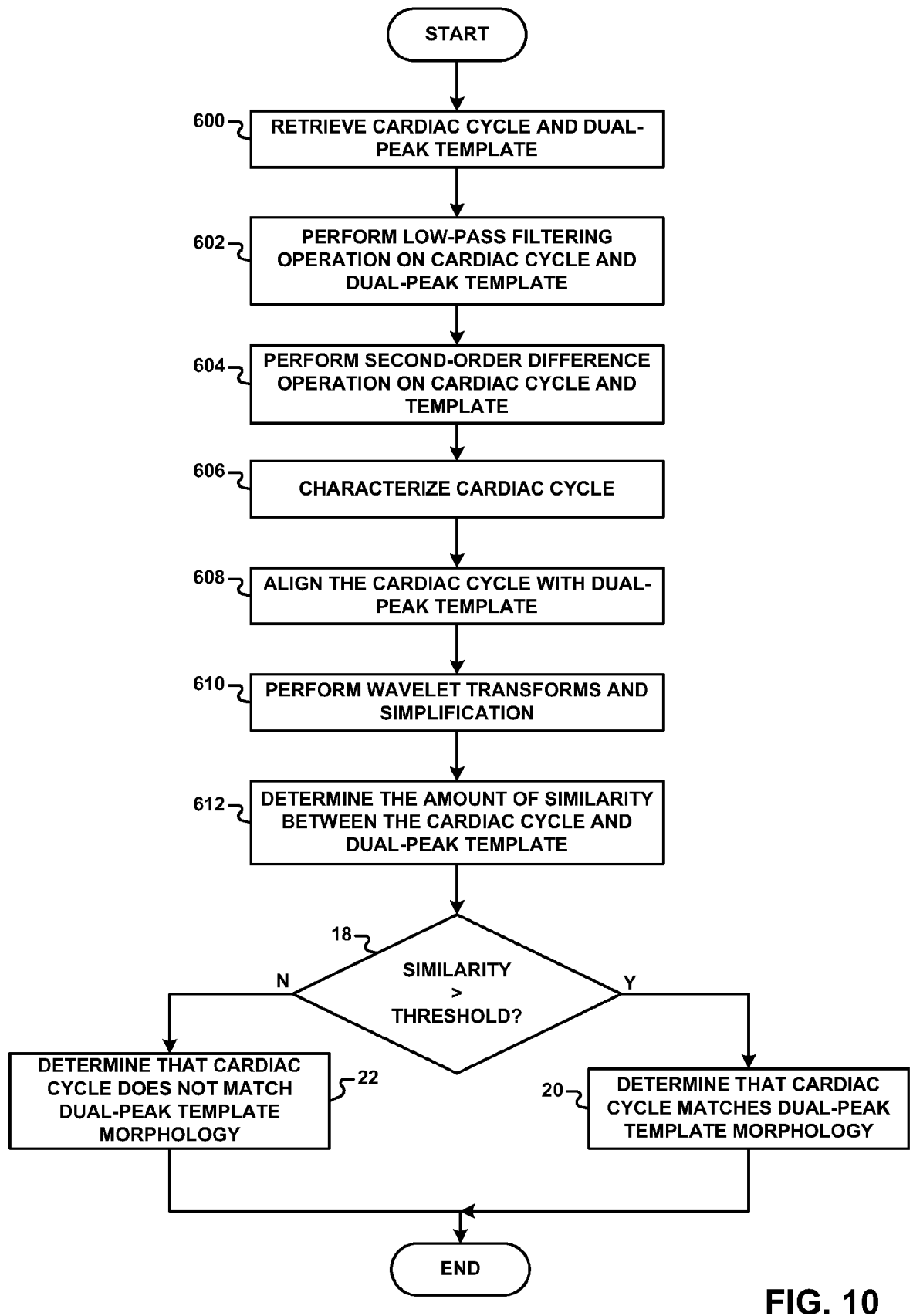
FIG. 10 shows a method for time-domain processing of a cardiac cycle and a dual-peak template prior to alignment.

Further details regarding implementation of the method described in FIG. 1 may be described hereinafter with respect to FIGS. 2-14. FIGS. 2-4 describe a system 100 and device (e.g., IMD 106) that may implement the method of FIG. 1. FIGS. 5-8 include further details of portions of the method of FIG. 1. FIGS. 9-10 describe using wavelet transformations and digital signal processing techniques to improve performance of the alignment and matching operations. FIGS. 11-14 illustrate alignment of various cardiac cycles and templates according to techniques of the present disclosure. FIG. 15 shows a method for identifying a rhythm of a plurality of cardiac cycles using the techniques of the present disclosure.

FIG. 1 shows a method for determining the morphology of a cardiac cycle using a dual-peak template. The dual-peak template may be generated prior to start of the method of FIG. 1 using a variety of different techniques. In some examples, the IMD may generate the dual-peak template, e.g., based on a previously acquired cardiac cycle. In other examples, a clinician may generate the dual-peak template using a computing device that is external to the IMD. The dual-peak template may be stored in memory of the IMD and retrieved at a later time for comparison to a cardiac cycle. The dual-peak template may be described as a template that includes first and second peaks having the same polarity. The first and second peaks may be referred to as alignment points since the peaks may be used as reference points for alignment with an acquired cardiac cycle. The alignment points may be referred to collectively as "template alignment points," and separately as first and second template alignment points. During an alignment operation, one of the template alignment points may be used as a reference point for alignment of a cardiac cycle.

The IMD may acquire and store one or more cardiac cycles during normal operation (10). For example, the IMD may include a memory that the IMD may use as a buffer to store recently acquired cardiac cycles. Such a buffer included in the IMD may be a first-in first-out (FIFO) buffer that buffers a predetermined amount of acquired cardiac electrical data (e.g., 12 cardiac cycles or more). The IMD may also store acquired cardiac cycles in a more long term storage region of the memory that is not continuously rewritten with the most recently acquired cardiac electrical data, as may be the case with the buffer portion of the memory. Instead, the long term storage region of the memory may include cardiac electrical data that has been stored in the more distant past, e.g., in response to detection of a tachyarrhythmia.

The IMD may characterize one of the stored cardiac cycles (12) as either a single-peak cycle or a dual-peak cycle in order to determine how to align the cardiac cycle with the dual-peak template during a comparison operation. The IMD may identify a plurality of morphological characteristics of the cardiac cycle, and may characterize the cardiac cycle based on the morphological characteristics. The morphological characteristics may include, but are not limited to, a number of peaks included in the cardiac cycle, a magnitude of the peaks, and the order in which the peaks occur (e.g., based on magnitude) if more than one peak is included in the cardiac cycle.

In general, the IMD may characterize a cardiac cycle as a dual-peak cycle when the cardiac cycle includes two peaks having the same polarity (e.g., voltage polarity) as the template peaks. The IMD may characterize a cardiac cycle as a single-peak cycle when the cardiac cycle may not be classified by the IMD as having two peaks of the same polarity as the template peaks. For example, the IMD may characterize a cardiac cycle as a single-peak cycle when the acquired cardiac cycle includes only a single identifiable peak value having the same polarity as the template peaks, but not a second identifiable peak value of the same polarity. An example method for characterizing a cardiac cycle is explained in greater detail with respect to FIG. 5.

A single-peak cycle may include one alignment point at the maximum peak value of the cardiac cycle. The alignment point of the single-peak cycle may referred to as the "single-peak alignment point." A dual-peak cycle may include two alignment points, one located at each of the two peaks of the dual-peak cycle. The alignment points of the dual-peak cycle may be referred to collectively as "dual-peak alignment points," and separately as first and second alignment points of the dual-peak cycle.

After characterization of the cardiac cycle in block 12, the IMD may align the cardiac cycle with the dual-peak template (14). The IMD may determine how to align the cardiac cycle with the dual-peak template based, in part, on the characterization of the cardiac cycle in block (12). If the IMD characterized the cardiac cycle as a single-peak cycle, the IMD may align the single-peak alignment point of the single-peak cycle with the alignment point corresponding to the largest peak of the dual-peak template. If the IMD characterized the cardiac cycle as a dual-peak cycle, the IMD may selectively align one of the alignment points of the dual-peak cycle and one of the template alignment points based on the morphologies (e.g., morphological similarities) of the dual-peak cycle and the dual-peak template. The IMD may align the dual-peak cycle with the dual-peak template based on the order of the two peaks of the dual-peak cardiac cycle and the order of the two peaks of the dual-peak template. In general, the IMD may align the dual-peak cycle with the dual-peak template in one of at least two ways.

As described herein, the order of two peaks (i.e., the "peak order") of the dual-peak cycle may refer to the order of the peaks of the dual-peak cycle by magnitude, and the peak order of the dual-peak template may refer to the order of the peaks of the dual-peak template by magnitude. The dual-peak cycle and the dual-peak template may exhibit one of two peak orders. A first peak order may refer to a scenario in which the larger of the two peaks occurs first, while a second peak order may refer to a scenario in which the smaller of the two peaks occurs first. Accordingly, a first peak order in the dual-peak cycle may describe a scenario where the alignment point of the larger peak occurs before the alignment point of the smaller peak within the dual-peak cycle. Alternatively, a second peak order in the dual-peak cycle may describe a scenario where the alignment point of the smaller peak occurs before the alignment point of the larger peak within the dual-peak cycle. In a similar manner, a first peak order in the dual-peak template may describe a scenario where the alignment point of the larger peak occurs before the alignment point of the smaller peak within the dual-peak template, and a second peak order in the dual-peak template may describe a scenario where the alignment point of the smaller peak occurs before the alignment point of the larger peak within the dual-peak template.

If the IMD determines that the two peaks of the dual-peak cycle and the two peaks of the dual-peak template have the same order, by magnitude, then the IMD may align the dual-peak template and the dual-peak cycle in a similar manner as the IMD would align a single-peak cycle with the dual-peak template (or a single-peak template). Specifically, the IMD may align the alignment point of the largest peak of the dual-peak cycle with the alignment point of the largest peak of the dual-peak template when the dual-peak cycle and the dual-peak template have the same peak order. If the IMD determines that the two peaks of the dual-peak cycle and the two peaks of the dual-peak template have different peak orders, the IMD may align the leftmost peaks of the dual-peak cycle and the dual-peak template.

Alignment of the cardiac cycle with the dual-peak template may be conceptually described as overlaying the cardiac cycle onto the dual-peak template and then shifting the cardiac cycle until an alignment point of the cardiac cycle and an alignment point of the dual-peak template are aligned. For example, when the cardiac cycle is characterized as a single-peak cycle, the IMD may overlay the single-peak cycle onto the dual-peak template and then shift the single peak cycle either to the left or right in order to align the single-peak alignment point of the single-peak cycle with the alignment point of the largest peak of the dual-peak template.

When the cardiac cycle is characterized as a dual-peak cycle, and the template is a dual-peak template, the IMD may overlay the dual-peak cycle onto the dual-peak template and then shift the dual-peak cycle in one of two ways. In the scenario where the peak order of dual-peak cycle and the peak order of the dual-peak template are the same, the IMD may shift the dual-peak cycle to either the right or the left in order to align the alignment point of the larger peak of the dual-peak cycle with the alignment point of the larger peak of the dual-peak template. In a scenario where the dual-peak cycle and the dual-peak template have different peak orders, the IMD may shift the dual-peak cycle to either the right or the left in order to align the leftmost peaks of the dual-peak cycle and the dual-peak template.

After alignment of the cardiac cycle with the dual-peak template in block (14), the IMD may determine the amount of similarity between the cardiac cycle and the dual-peak template (16). In some examples, the IMD may determine a matching score that indicates the amount of similarity between the cardiac cycle and the dual-peak template. In other words, the matching score may be a quantified amount of similarity between the cardiac cycle and the dual-peak template that indicates how well the cardiac cycle matches the dual-peak template. In some examples, as described with respect to FIG. 10, the IMD may perform a transform (e.g., a wavelet transform) on the cardiac cycle and the dual-peak template, and then determine the matching score based on a comparison of the transformed cardiac cycle and the transformed dual-peak template.

A larger matching score may indicate a greater amount of similarity between the cardiac cycle and the dual-peak template, while a smaller matching score may indicate a lesser amount of similarity between the cardiac cycle and the dual-peak template. The matching score may be expressed as a percentage. A 100% matching score may indicate an exact match between the cardiac cycle and the dual-peak template, while a matching score of less than 100% may indicate a lesser amount of similarity.

After determining the amount of similarity (e.g., the matching score) between the cardiac cycle and the dual-peak template in block (16), the IMD may determine whether the amount of similarity is greater than a threshold amount of similarity (18). If the amount of similarity is greater than the threshold amount of similarity, the IMD may determine that the cardiac cycle matches the dual-peak template morphology (20). In terms of matching score, if the matching score determined in block (16) is greater than a threshold matching score, the IMD may determine that the cardiac cycle matches the dual-peak template morphology (20). If the amount of similarity is less than the threshold amount of similarity, the IMD may determine that the cardiac cycle does not match the dual-peak template morphology (22). In terms of matching score, if the matching score is less than the threshold matching score, the IMD may determine that the cardiac cycle does not match the dual-peak template morphology (22). In some examples, the IMD may classify the cardiac cycle based on whether the cardiac cycle matches the dual-peak template. In examples where the dual-peak template is based on a normal cardiac conduction pattern, the IMD may determine that the conduction pattern of the cardiac cycle may also be a normal conduction pattern when the IMD detects a match at block (20). Alternatively, the IMD may determine that the conduction pattern of the cardiac cycle does not correspond to a normal conduction pattern when the IMD detects a mismatch at block (22).

A more detailed explanation of an IMD that implements the method of FIG. 1, along with a more detailed explanation of the method of FIG. 1 and the use of the method in discriminating between different types of tachyarrhythmia is described hereinafter.

FIG. 2 shows an example system 100 that may be used to diagnose conditions of and provide therapy to a heart 102 of a patient 104. System 100 includes an IMD 106. For example, IMD 106 may be an implantable pacemaker, cardioverter, and/or defibrillator that monitors electrical activity of heart 102 and provides electrical stimulation to heart 102.

IMD 106 includes a housing 108 and a connector block 110. Housing 108 and connector block 110 may form a hermetic seal that protects components of IMD 106. IMD 106 is coupled to leads 112, 114, and 116 via connector block 110. Leads 112, 114, 116 extend into heart 102. Right ventricular lead 114 extends into right ventricle 118. Left ventricular coronary sinus lead 116 extends into the coronary sinus to a region adjacent to the free wall of left ventricle 120. Right atrial lead 112 extends into right atrium 122.

Housing 108 may enclose an electrical sensing module that monitors electrical activity of heart 102, and may also enclose a signal generator module that generates therapeutic stimulation, such as cardiac pacing pulses, ATP therapy, cardioversion therapy, and/or defibrillation therapy. Leads 112, 114, 116 are coupled to the signal generator module and the electrical sensing module of IMD 106 via connector block 110.

FIG. 3 shows a more detailed view of IMD 106 and leads 112, 114, 116. IMD 106 includes a housing electrode 124, which may be formed integrally with an outer surface of housing 108 of IMD 106 or otherwise coupled to housing 108. Although a single housing electrode 124 is illustrated in FIGS. 2-3, IMD 106 may include more or less than a single housing electrode 124.

Leads 112, 114, 116 include electrodes 126-1-126-9 (collectively "electrodes 126"). Lead 114 includes bipolar electrodes 126-1, 126-2 which are located in right ventricle 118. Lead 116 includes bipolar electrodes 126-3, 126-4 which are located in coronary sinus 128. Lead 112 includes bipolar electrodes 126-5, 126-6 which are located in right atrium 122. Electrodes 126-1, 126-3, 126-5 may take the form of ring electrodes. Electrodes 126-2, 126-4, 126-6 may take the form of, for example, helix tip electrodes or small circular electrodes at the tip of a tined lead or other fixation element. Leads 112, 114, 116 also include elongated electrodes 126-7, 126-8, 126-9, respectively, which may take the form of a coil.

Although three leads 112, 114, 116, each including three electrodes, are illustrated, other configurations of leads and electrodes are contemplated.

IMD 106 may sense electrical activity of heart 102 and/or deliver electrical stimulation to heart 102 via electrodes 124, 126. IMD 106 may sense electrical activity using any combination of electrodes 124, 126. For example, IMD 106 may sense electrical activity via any bipolar combination of electrodes 126. Furthermore, any of electrodes 126 may be used for unipolar sensing in combination with housing electrode 124. IMD 106 may deliver pacing pulses via electrodes 124, 126 using a unipolar or bipolar combination of electrodes 124, 126. IMD 106 may deliver cardioversion pulses and/or defibrillation pulses to heart 102 via any combination of elongated electrodes 126-7, 126-8, 126-9, and housing electrode 124.

Using the signal generator module and the electrical sensing module, IMD 106 may provide pacing pulses to heart 102 based on the electrical signals sensed within heart 102. IMD 106 may also provide ATP therapy, cardioversion, and/or defibrillation therapy to heart 102 based on the electrical signals sensed within heart 102. For example, IMD 106 may detect an arrhythmia of heart 102, such as VT or VF, and deliver ATP therapy, cardioversion, or defibrillation therapy to heart 102 in response to the detection of VT/VF.

Referring back to FIG. 2, system 100 may include a programmer 130. Programmer 130 may be a handheld computing device, desktop computing device, a networked computing device, etc. Programmer 130 may include a computer-readable storage medium having instructions that cause a processor of programmer 130 to provide the functions attributed to programmer 130 in the present disclosure. Programmer 130 may include a telemetry head (not shown). IMD 106 and programmer 130 may wirelessly communicate with one another, e.g., transfer data between one another, via the telemetry head. For example, IMD 106 may send data to programmer 130, and programmer 130 may retrieve data stored in IMD 106 and/or program IMD 106.

Data retrieved from IMD 106 using programmer 130 may include cardiac EGMs stored by IMD 106 that indicate electrical activity of heart 102. Data may also include marker channel data that indicates the occurrence and timing of sensing, diagnosis, and therapy events associated with IMD 106. Additionally, data may include information regarding the performance or integrity of IMD 106 or other components of diagnostic system 100, such as leads 112, 114, 116, or a power source of IMD 106. Data transferred to IMD 106 using programmer 130 may include, for example, values for operational parameters, electrode selections used to deliver defibrillation pulses, waveform selections used for defibrillation pulses, and/or dual-peak templates generated by a clinician.

FIG. 4 shows a functional block diagram of an example IMD 106. IMD 106 includes a processing module 132, memory 134, a signal generator module 136, an electrical sensing module 138, a communication module 140, and a power source 142, such as a battery, e.g., a rechargeable or non-rechargeable battery. In some examples, IMD 106 may include one or more sensors (e.g., sensor 144) with which processing module 132 may communicate. For example, sensor 144 may comprise at least one of a motion sensor (e.g., an accelerometer or piezoelectric element) and a heart sound sensor. Processing module 132 may determine, for example, an activity level of patient 104 and a heart rate of patient 104 based on data measured by sensor 144.

Modules included in IMD 106 represent functionality that may be included in IMD 106 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Processing module 132 may communicate with memory 134. Memory 134 may include computer-readable instructions that, when executed by processing module 132, cause processing module 132 to perform the various functions attributed to processing module 132 herein. Memory 134 may include any volatile, non-volatile, magnetic, or electrical media, such as RAM, ROM, NVRAM, EEPROM, Flash memory, or any other digital media.

Processing module 132 may communicate with signal generator module 136 and electrical sensing module 138. Signal generator module 136 and electrical sensing module 138 are electrically coupled to electrodes 126 of leads 112, 114, 116 and housing electrode 124. Electrical sensing module 138 is configured to monitor signals from electrodes 124, 126 in order to monitor electrical activity of heart 102. Electrical sensing module 138 may selectively monitor any bipolar or unipolar combination of electrodes 124, 126. In one example, electrical sensing module 138 may monitor electrical signals generated between electrodes 126-1, 126-2 (which may be referred to as a Vtip-Vring configuration due to the inclusion of a ventricular tip electrode and a ventricular ring electrode) and electrodes 124, 126-7 (which may be referred to as HVA-HVB, with the "HV" in HVA and HVB designating "high-voltage" as electrodes 124 and 126-7 are electrodes that may be used to deliver high-voltage therapies, e.g., cardioversion or defibrillation). The electrical signals monitored between electrodes 124, 126-7 may be referred to as the far-field EGM. Although the EGMs acquired by electrical sensing module 138 may be described herein as received from electrodes 126-1, 126-2 (Vtip-Vring) and 124, 126-7 (HVA-HVB), other electrode combinations may be used to acquire EGMs for analysis according to the present disclosure.

Signal generator module 136 may generate and deliver electrical stimulation therapy to heart 102 via electrodes 124, 126. Electrical stimulation therapy may include at least one of pacing pulses, ATP therapy, cardioversion therapy, and defibrillation therapy. Processing module 132 may control signal generator module 136 to deliver electrical stimulation therapy to heart 102 according to one or more therapy programs, which may be stored in memory 134. For example, processing module 132 may control signal generator module

136 to deliver pacing pulses to heart 102 based on one or more therapy programs and signals received from electrical sensing module 138. In other examples, processing module 132 may control signal generator module 136 to deliver at least one of ATP therapy, cardioversion therapy, and defibrillation therapy when processing module 132 detects a tachyarrhythmia.

For example, in the event that processing module 132 detects a tachyarrhythmia, processing module 132 may load an ATP regimen from memory 134, and control signal generator module 136 to implement the ATP regimen. In other examples, processing module 132 may implement a cardioversion regimen or a defibrillation regimen upon detection of a tachyarrhythmia. Signal generator module 136 may include a high voltage charge circuit and a high voltage output circuit when signal generator module 136 is configured to generate and deliver defibrillation therapy to heart 102.

Communication module 140 includes any suitable hardware, firmware, software or any combination thereof for communicating with another device, such as programmer 130 and/or a patient monitor. Under the control of processing module 132, communication module 140 may receive downlink telemetry from and send uplink telemetry to programmer 130 and/or a patient monitor with the aid of an antenna (not shown) in IMD 106.

Electrical sensing module 138 may include signal conditioning circuits, e.g., amplification and filtering circuits that amplify and filter cardiac electrical signals received from electrodes 124, 126. Electrical sensing module 138 may include analog-to-digital (A/D) conversion circuits that digitize the conditioned cardiac electrical signals. The digitized data generated by the A/D circuits included in electrical sensing module 138 may be referred to as "raw data." In some examples, the A/D circuits may include an 8-bit A/D converter that samples conditioned cardiac electrical signals at approximately 256 Hz.

Processing module 132 may receive raw data from electrical sensing module 138 and detect cardiac events based on the raw data. For example, processing module 132 may analyze the raw data and detect arrhythmias (e.g., VT/VF) using any suitable arrhythmia detection algorithm. In one example, processing module 132 may detect tachyarrhythmias using a rate-based detection algorithm in which processing module 132 monitors R-R intervals and identifies a tachyarrhythmia when a predetermined ratio of R-R intervals are shorter than a threshold interval.

Processing module 132 may generate marker channel data based on analysis of the raw data. Marker channel data may include data that indicates the occurrence and timing of sensing, diagnosis, and therapy events associated with IMD 106. Processing module 132 may store the generated marker channel data in memory 134. Although not illustrated, in some examples, marker channel data may include information regarding the performance or integrity of IMD 106 or other components of system 100, such as leads 112, 114, 116, or power source 142.

Processing module 132 may store raw data and marker channel data in memory 134. For example, processing module 132 may continuously store raw data from one or more electrode combinations in memory 134 as the raw data is received from electrical sensing module 138. In this manner, processing module 132 may use memory 134 as a buffer to store a predetermined amount of raw data. In some examples, processing module 132 may store raw data corresponding to a predetermined number of cardiac cycles, e.g., 12 cycles. In other examples, processing module 132 may store a predetermined number of samples of raw data, e.g., processing module 132 may stored raw data for a predetermined period of time. Processing module 132 may perform analysis on the raw data stored in memory 134. For example, analysis may include detection of tachyarrhythmia, determination of cardiac cycle morphology using the dual-peak template, generation of marker channel data, and the like, as described above.

Processing module 132 may determine the morphology of one or more cardiac cycles using raw data stored in memory 134. Each cardiac cycle analyzed by processing module 132 may refer to the raw data of sampled cardiac electrical activity that occurs from the beginning of one heartbeat to the beginning of the next heartbeat. Processing module 132 may identify and store a cardiac cycle using a variety of techniques. In one example, processing module 132 may identify an event in the cardiac cycle, such as a QRS complex (e.g., an R wave), and store a window of raw data both before and after the event. For example, processing module 132 may store a predetermined number of raw data points before and after the identified event, e.g., approximately 25 data points before the event and 25 data points after the event, for a total of approximately 50 stored raw data points for each cardiac cycle. Accordingly, in some examples, each cardiac cycle stored in memory 134 may include approximately 50 raw data points. In examples where the A/D converter of electrical sensing module 138 samples cardiac electrical signals at approximately 256 Hz, processing module 132 may store approximately 200 ms of sampled cardiac electrical activity for each cardiac cycle.

Example raw data generated by electrical sensing module 138 based on sensed cardiac electrical activity is illustrated in FIGS. 8 and 11-14. Although processing module 132, as described herein, may perform comparisons between far-field EGM data and the dual-peak template, in other examples, processing module 132 may perform comparisons between raw data other than far-field EGM data. For example, processing module 132 may perform comparisons between the dual-peak template and raw data retrieved from Vtip-Vring data, or any other suitable combination of electrodes 124, 126. In some examples, far-field EGM data may be more suitable for analysis, but this may vary on a patient to patient basis.

The example method of FIG. 1, in which the morphology of a single cardiac cycle is determined, is now described with respect to the detailed example IMD 106 of FIG. 4. Memory 134 may include a dual-peak template. As described above, the dual-peak template may have been generated by processing module 132 or generated on an external computing device and subsequently downloaded into memory 134 via communication module 140.

Prior to the start of the method of FIG. 1, processing module 132 may have received raw data from electrical sensing module 138 and stored raw data in memory 134 during normal operation (10). In some examples, processing module 132 may have buffered a predetermined number of cardiac cycles in memory 134. In other examples, processing module 132 may have detected a tachyarrhythmia and stored cardiac cycles included in the detected tachyarrhythmia in memory 134 for later analysis. Using the method of FIG. 1, processing module 132 may selectively determine the morphology of either the cardiac cycles buffered in memory 134, or the cardiac cycles that are stored long term within memory 134, e.g., in response to detection of a tachyarrhythmia.

Processing module 132 may characterize one of the cardiac cycles stored in memory 134 as either a single-peak cycle or a dual-peak cycle (12). During the characterization at block (12), processing module 132 may determine a set of morphological characteristics of the cardiac cycle which may include, but are not limited to, a number of peaks included in the cardiac cycle, a magnitude of the peaks, and the order in which the peaks occur (e.g., based on magnitude) if more than one peak is present.

Figure 5:
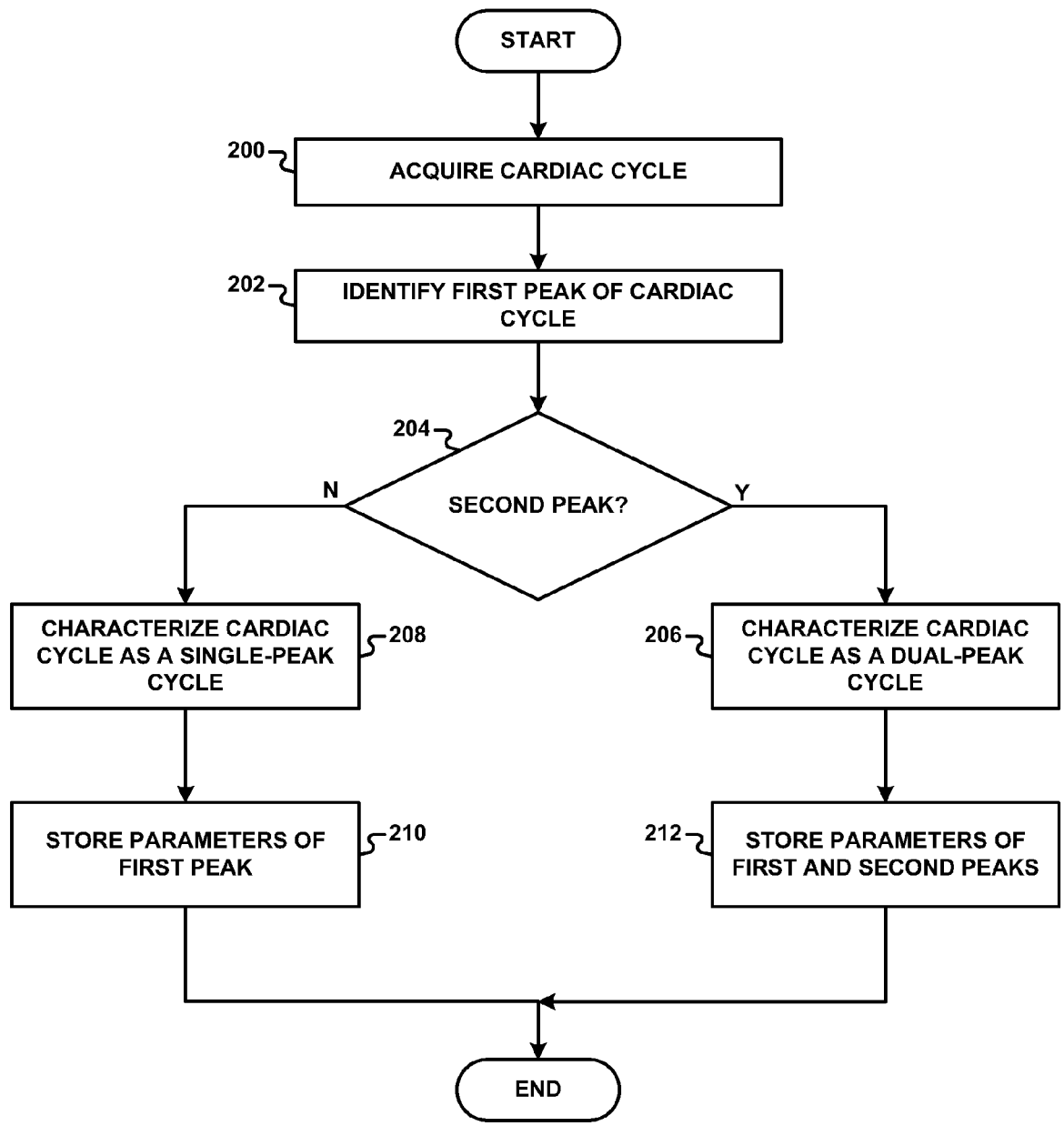
FIG. 5 shows an example method for characterizing a cardiac cycle as either a single-peak cycle or a dual-peak cycle.

Referring now to FIG. 5, an example method for characterizing a cardiac cycle as either a single-peak cycle or a dual-peak cycle according to block (12) of FIG. 1 is shown. Initially, processing module 132 may acquire a cardiac cycle from memory 134 (200). Processing module 132 may characterize this cardiac cycle acquired in block (200) as either a single-peak cycle or a dual-peak cycle according to the method of FIG. 5.

Processing module 132 may identify the first peak of the cardiac cycle (202) by scanning the cardiac cycle and identifying the largest peak of the cardiac cycle having the same polarity as the larger and smaller template peaks. In some examples, the largest peak may be described as the largest value that occurs at a zero slope region of the cardiac cycle having the same polarity as the template peaks. The first peak may be either a positive or a negative value, depending on the polarity of the template peaks.

The first peak, identified in block (202), may be the global maximum value of the cardiac cycle, e.g., either the largest positive value within the cardiac cycle or the largest negative value within the cardiac cycle, since such a global maximum value of a cardiac cycle typically occurs at peak point within the cardiac cycle. For example, with respect to FIG. 12A, the first peak value may correspond to point 171 of cardiac cycle 172.

After identifying the first peak, processing module 132 may determine whether a second peak is present in the cardiac cycle (204) having the same polarity as the template peaks. Generally, the second peak in the cardiac cycle may be described as another peak in the cardiac cycle having a lesser (or equal) value than the first peak, and having the same polarity as the first peak.

In some examples, processing module 132 may impose further constraints on what processing module 132 may identify as a second peak. For example, processing module 132 may impose constraints on the magnitude of the second peak and the distance from the second peak to the first peak. For example, processing module 132 may require that the second peak value is greater than a minimum threshold value (e.g., half the magnitude of the first peak). Such a constraint may assure that the peak of the cardiac cycle identified as the second peak is truly a distinct peak in relation to the first peak, and not a morphology of the cardiac cycle that may be indicative of drift or another physiologically insignificant phenomenon. In these examples, processing module 132 may identify the second peak when processing module 132 identifies a peak in the cardiac cycle that has a magnitude that is less than or equal to the first peak, that has a magnitude that is greater than the minimum threshold value, and that has the same polarity as the first peak.

In some examples, processing module 132 may impose a constraint on the distance between the first and second peaks. For example, processing module 132 may require that the second peak is a sufficient distance from the first peak (e.g., two or more samples from the first peak). Such a constraint may assure that the second peak is truly a distinct peak in relation to the first peak, and not an artifact (e.g., noise spike or other physiologically insignificant signal) of the cardiac cycle that is included on a slope on either side of the first peak. In these examples, processing module 132 may identify the second peak when processing module 132 identifies a peak in the cardiac cycle that has a magnitude that is less than or equal to the first peak, that has a magnitude that is greater than a minimum threshold value (e.g., half of the magnitude of the first peak), that is a sufficient distance (e.g., two or more samples) from the first peak, and that has the same polarity as the first peak. The dual-peak template may include similar constraints as described above. For example, the peaks of the dual-peak template may be separated by two or more samples.

If processing module 132 identifies the second peak in the cardiac cycle, processing module 132 may characterize the cardiac cycle as a dual-peak cycle (206). If processing module 132 does not identify a second peak, processing module 132 may characterize the cardiac cycle as a single-peak cycle (208).

Processing module 132 may store parameters of the cardiac cycle in memory 134. If processing module 132 characterizes the cardiac cycle as a single-peak cycle, processing module 132 may store the location (i.e., the sample number within the cardiac cycle) at which the single peak occurs within the cardiac cycle (210). This location may be referred to as the location of the single-peak alignment point. A location within a cardiac cycle may refer to the sample number of the cardiac cycle. For example, assuming a cardiac cycle includes n discrete samples of cardiac electrical activity, the cardiac cycle may include n locations, ranging for example from location 0 to location (n−1), where the $0^{th}$ sample is the first location in the cardiac cycle and the $(n-1)^{th}$ location is the $n^{th}$ sample in the cardiac cycle. As described above, a cardiac cycle may include approximately 50 samples. If a stored cardiac cycle includes 50 samples, n=50, and the locations within the cardiac cycle range from location 0 to location 49, each of the 50 locations corresponding to a different sampled voltage.

In examples where processing module 132 characterized the cardiac cycle as a dual-peak cycle, processing module 132 may store the locations of the first and second peaks along with the corresponding magnitudes of the first and second peaks (212). Processing module 132 may use the peak locations and amplitudes to determine how to align the dual-peak cycle with the dual-peak template.

Referring back to FIG. 1, after characterizing the cardiac cycle at block (12), processing module 132 may determine how to align the cardiac cycle with the dual-peak template based on whether the cardiac cycle was classified as a single-peak cycle or a dual-peak cycle. Processing module 132 may then align the cardiac cycle with the dual-peak template (16).

Figure 6:
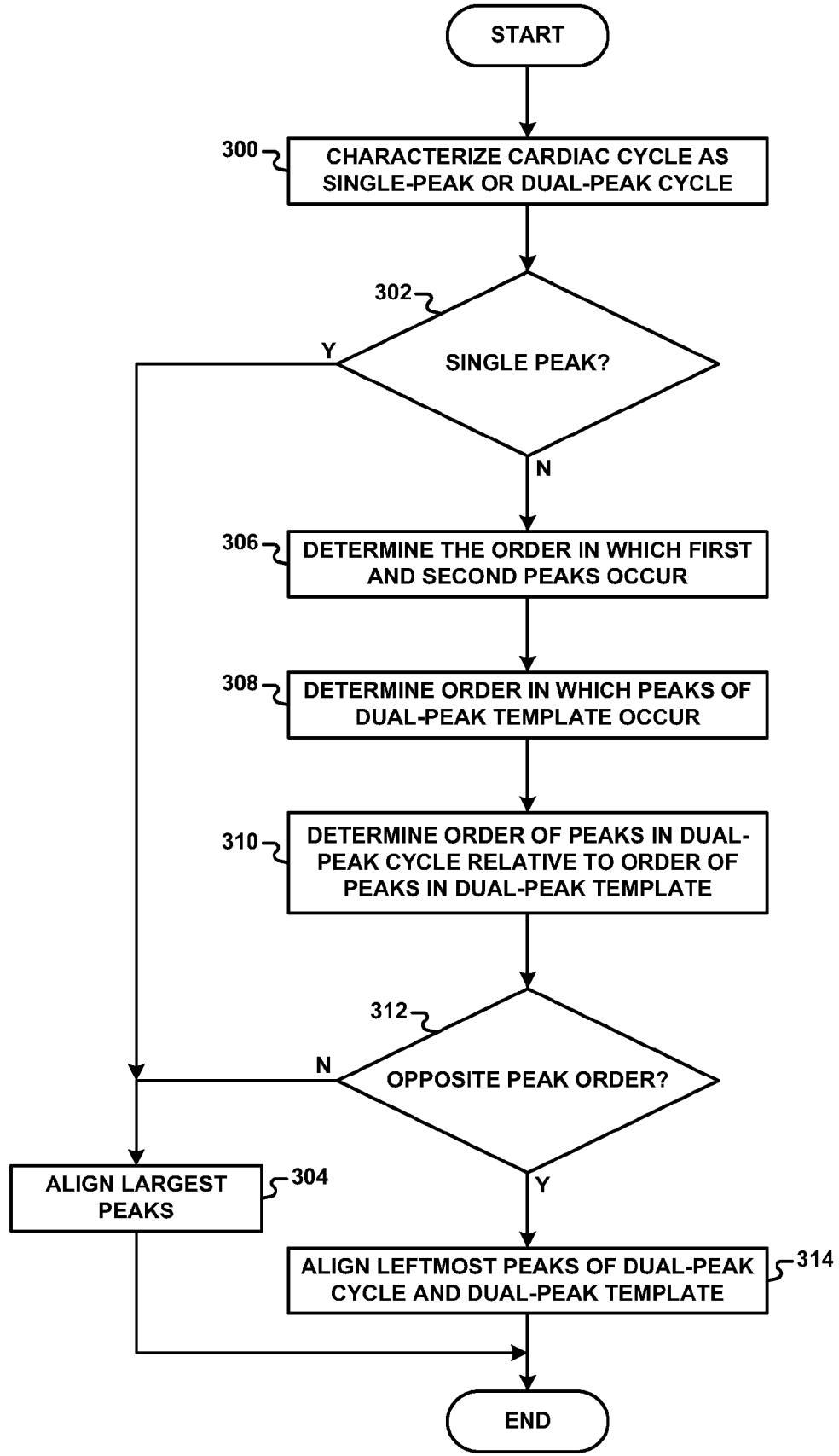
FIG. 6 shows a method for aligning a cardiac cycle with a dual-peak template.

FIG. 6 shows an example method for aligning a cardiac cycle with a dual-peak template. Prior to the method of FIG. 6, processing module 132 may have acquired a cardiac cycle. Initially, processing module 132 characterizes the cardiac cycle as one of a single-peak cycle or a dual-peak cycle (300), as described above with respect to FIG. 5.

If processing module 132 determines that the cardiac cycle is a single-peak cycle at block (302), processing module 132 aligns the single-peak alignment point of the single-peak cycle with the larger peak of the dual-peak template (304). If processing module 132 determines that the cardiac cycle is not a single peak cycle at block (300), i.e., if the cardiac cycle is a dual-peak cycle, processing module 132 determines an order in which the first and second peaks of the dual-peak cycle occur (306). As described above, the order in which the first and second peaks occur may refer to the order that the peaks occur based on the magnitude of the peaks.

Processing module 132 then determines an order in which the first and second peaks of the dual-peak template occur (308) then determines the order of the peaks in the dual-peak cycle relative to the order of the peaks in the dual-peak template (310). In some examples, processing module 132 may determine that the order of the peaks in the dual-peak cycle is the same as the order of the peaks in the dual-peak template. For example, processing module 132 may determine that the peak order is the same if the largest peaks of the dual-peak cycle and the dual-peak template occur first. As another example, processing module 132 may determine that the peak order is the same if the smaller peaks in the dual-peak cycle and the dual-peak template occur first. If processing module 132 determines that the order of the peaks in the dual-peak cycle is the same as the order of the peaks in the dual-peak template at block (312), then processing module 132 may align the largest peak of the dual-peak cycle with the largest peak of the dual-peak template (304).

In other examples, processing module 132 may determine that the order of the peaks in the dual-peak cycle is opposite to the order of the peaks in the dual-peak template. For example, processing module 132 may determine that the order of the peaks is opposite if the larger peak in the dual-peak cycle occurs first and the smaller peak in the dual-peak template occurs first. As another example, processing module 132 may determine that the order of the peaks is opposite if the smaller peak in the dual-peak cycle occurs first and the larger peak in the dual-peak template occurs first. If processing module 132 determines that the order of the peaks in the dual-peak cycle is opposite to the order of the peaks in the dual-peak template at block (312), then processing module 132 may align the leftmost peaks of the dual-peak cycle and the dual-peak template (314).

In some examples, not illustrated in the method of FIG. 6, processing module 132 may impose further constraints on alignment between the leftmost peaks of the dual-peak cycle and the dual-peak template. For example, in order for processing module 132 to align the leftmost peaks in block (314), processing module 132 may require that the distance between the peaks of the dual-peak cycle is similar to the distance between the peaks of the dual-peak template, e.g., within a four sample difference. If the distance between the peaks of the dual-peak cycle and the dual-peak template are not similar, then processing module 132 may align the largest peaks of the dual-peak cycle and the dual-peak template according to block (304).

Figure 7:
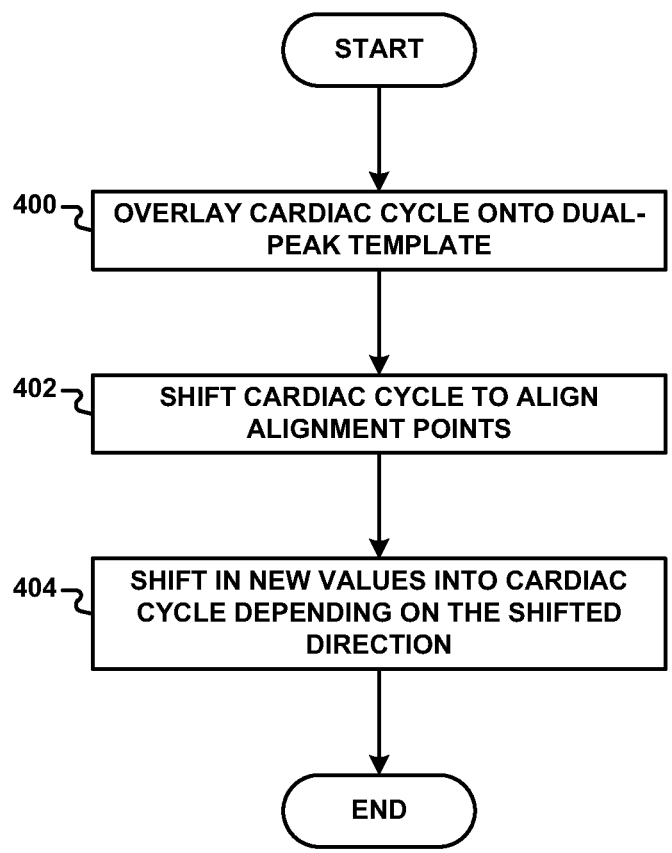
FIG. 7 shows a method for overlaying a cardiac cycle onto a dual-peak template and shifting the cardiac cycle relative to the dual-peak template.

FIG. 7 shows an example method for overlaying a cardiac cycle onto a dual-peak template and shifting the cardiac cycle relative to the dual-peak template. As described above, a cardiac cycle (e.g., single-peak or dual-peak) and the dual-peak template may each include arrays of discrete points (e.g., approximately 50). Conceptually, during alignment, processing module 132 may first overlay (e.g., match up) points of the cardiac cycle with points of the dual-peak template (400). Processing module 132 may then shift the points of the cardiac cycles either to the left or right relative to the dual-peak template points in order to match alignment points (i.e. peaks) of the cardiac cycle with alignment points (i.e., peaks) of the dual-peak template (402). Processing module 132 may shift new values into the cardiac cycle when the cardiac cycle is shifted to align with the dual-peak template (404). In some examples, processing module 132 may shift new values into the cardiac cycle at the left side of the cardiac cycle when the cardiac cycle is shifted to the right during alignment. Alternatively, processing module 132 may shift new values into the cardiac cycle at the right side of the cardiac cycle when the cardiac cycle is shifted to the left during alignment.

In some examples, the new values shifted into the cardiac cycle may be the same as either the initial rightmost or initial leftmost value of the cardiac cycle. For example, when the cardiac cycle is shifted to the left, the new values shifted into the cardiac cycle at the right side of the cardiac cycle may be equal to the initial rightmost value of the cardiac cycle. Alternatively, when the cardiac cycle is shifted to the right, the new values shifted into the cardiac cycle at the left side of the cardiac cycle may be equal to the initial leftmost value of the cardiac cycle. In other examples, the new values shifted into the cardiac cycle may include values other than the initial rightmost or initial leftmost values of the cardiac cycle. For example, the new values shifted into the cardiac cycle may be a baseline value (e.g., 0 mV) of the cardiac cycle, regardless of the direction the cardiac cycle is shifted.

Figure 8A:
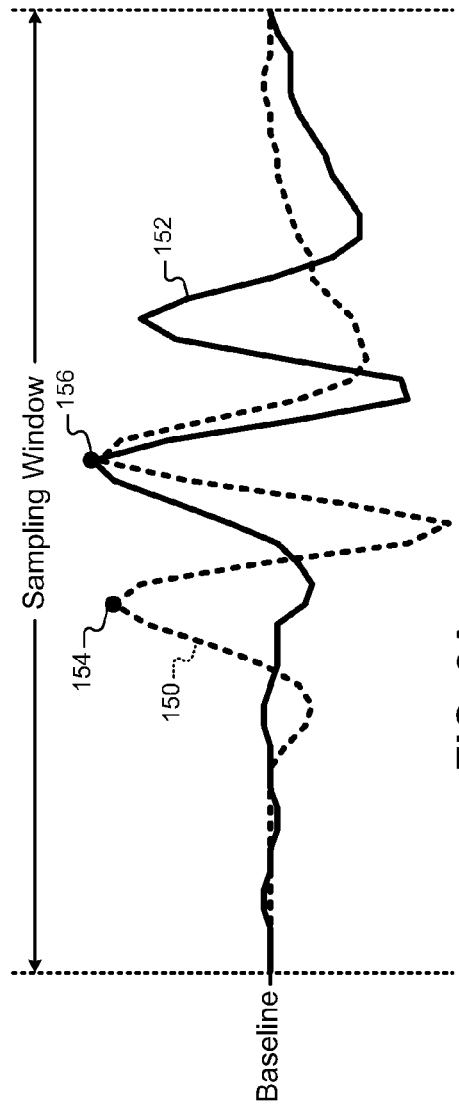
FIGS. 8A-8B illustrate overlaying a cardiac cycle onto a dual-peak template and shifting of the cardiac cycle relative to the dual-peak template.
Figure 8B:
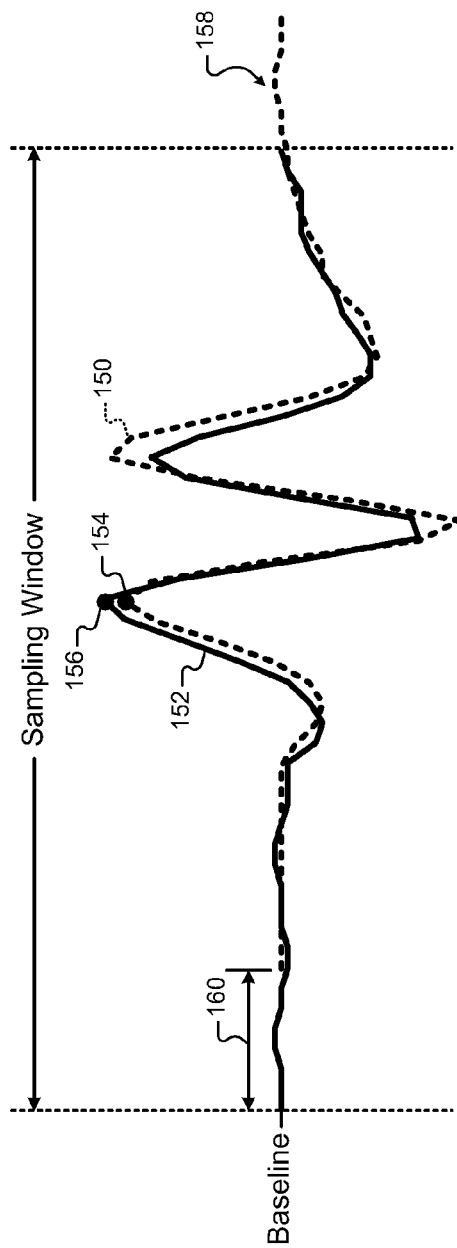

FIGS. 8A-8B illustrate overlaying a cardiac cycle onto a dual-peak template and shifting of the cardiac cycle relative to the dual-peak template. FIG. 8A shows an example dual-peak cycle 150 (dotted line) overlaid onto an example dual-peak template 152 (solid line). The "Sampling Window" added to FIGS. 8A and 8B graphically demonstrates the shifting in and out of values from dual-peak cycle 150. The "Sampling Window" may illustrate the bounds of the dual-peak cycle 150 as originally sampled by electrical sensing module 138. The "Sampling Window" may include approximately 50 sample points.

Dual-peak cycle 150 includes alignment point 154 and dual-peak template 152 includes template alignment point 156. Alignment point 154 and template alignment point 156 may have been selected for alignment by processing module 132 according to the techniques described above. For example, note that dual-peak template 152 has a peak order in which the larger peak occurs to the left of (i.e., before) the smaller peak, while dual-peak cycle 150 has a peak order in which the smaller peak occurs to the left of (i.e., before) the larger peak. In other words, the peak order of the dual-peak cycle 150 is opposite to the peak order of the dual-peak template 152. Therefore, processing module 132 may select the leftmost peaks of the dual-peak cycle 150 and the dual-peak template 152 for alignment. As illustrated in FIGS. 8A-8B, alignment point 154 and template alignment point 156 are the leftmost peaks of the dual-peak cycle 150 and the dual-peak template 152, respectively.

When dual-peak cycle 150 is initially overlaid onto dual-peak template 152, template alignment point 156 is positioned to the right of alignment point 154. Processing module 132 may therefore shift alignment point 154 to the right in order to align alignment point 154 with template alignment point 156. FIG. 8B shows dual-peak cycle 150 shifted to the right such that alignment point 154 is aligned with template alignment point 156. After processing module 132 shifts dual-peak cycle 150, a portion of the originally sampled data points of dual-peak cycle 150 are shifted outside of the sampling window, as illustrated at 158. In order to replace sampling points on the left side of dual-peak cycle 150, so that the dual-peak cycle 150 includes data points for determination of the matching score between the dual-peak cycle 150 and dual-peak template 152, processing module 132 may add points onto the left side of the dual-peak cycle 150 in the region illustrated at 160. As described above, processing module 132 may add points to region 160 that are equal to the leftmost point of the dual-peak cycle 150, as originally sampled. In other examples, processing module 132 may add points to region 160 that are equal to the baseline value of the dual-peak cycle 150 (e.g., 0 mV).

Referring back to FIG. 1, after alignment of the cardiac cycle with the dual-peak template in block (14), processing module 132 may determine an amount of similarity between the cardiac cycle and the dual-peak template (16). Processing module 132 may quantify the amount of similarity between the cardiac cycle and the dual-peak template as a matching score. Processing module 132 may determine the matching score in a variety of different ways. In general, a matching score may be a quantitative measure that identifies the amount of similarity between the cardiac cycle and the template. A higher matching score may indicate a greater similarity between the cardiac cycle and the dual-peak template, while a lower matching score may indicate a lesser amount of similarity between the cardiac cycle and the dual-peak template, as described above.

Two general techniques for determining the matching score are described herein. The two general techniques include a time domain matching technique and a wavelet domain matching technique. Processing module 132 may perform a time domain matching technique by comparing the aligned cardiac cycle and dual-peak template in the time domain, i.e., comparing the samples of the cardiac cycle and dual-peak template as sampled. In some examples, processing module 132 may determine the matching score by performing a point by point comparison of the cardiac cycle with the dual-peak template. Generally, the closer the cardiac cycle matches the dual-peak template on a point-by-point basis, the higher matching score that may be achieved. In one example, if the points of the cardiac cycle exactly matched the points of the dual-peak template, processing module 132 would compute a matching score of 100%. During a typical matching operation, however, the points of the cardiac cycle deviate from the dual-peak template on a point-by-point basis. A greater amount of deviation between the points of the cardiac cycle and the dual-peak template may result in a lower matching score (i.e., lower than 100%).

In examples where the cardiac cycle and the dual-peak template each include 50 points, processing module 132 may make 50 point-by-point comparisons in the time domain and determine the matching score based on the 50 point-by-point comparisons. Instead of or in addition to performing comparisons in the time domain, processing module 132 may perform transform operations and compression operations on the cardiac cycle and the dual-peak templates to reduce the computational burden of the 50 point comparison that may be performed in the time domain.

In some examples, processing module 132 may perform a wavelet transform (e.g., a Haar wavelet transform) on both the cardiac cycle and the dual-peak template after alignment. The Haar wavelet transform may be used since the Haar wavelet transform may be computed very efficiently compared to other wavelet transforms. The output of the Haar wavelet transform may be a plurality of wavelet coefficients, e.g., one coefficient for each sample in the time domain. Accordingly, in some examples, processing module 132 may perform a Haar wavelet transform on the cardiac cycle and the dual-peak template to generate a plurality of wavelet coefficients (e.g., 50 coefficients) for the cardiac cycle and another plurality of wavelet coefficients (e.g., 50 coefficients) for the dual-peak template. In some examples, processing module 132 may compare the transforms of the cardiac cycle and the dual-peak template in the wavelet domain without performing further compression operations on the transforms of the cardiac cycle and the dual-peak template.

In other examples, processing module 132 may compress the transformed cardiac cycle and the transformed dual-peak template. Generally, the wavelet coefficients for a cardiac cycle may be simplified, depending on the relative magnitudes of the wavelet coefficients for the cardiac cycle. Processing module 132 may simplify the wavelet transform coefficients by setting some of the wavelet coefficients to zero if the wavelet coefficients are not sufficiently large relative to other wavelet coefficients of the cardiac cycle. In some examples, processing module 132 may set a wavelet coefficient to zero when the magnitude of the wavelet coefficient is a threshold amount smaller than other wavelet coefficients of the cardiac cycle. For example, processing module 132 may set a wavelet coefficient to zero if the absolute value of the wavelet coefficient is less than a predetermined fractional amount of the maximum wavelet coefficient (e.g., less than $\frac{1}{8}$, $\frac{1}{16}$ or $\frac{1}{32}$ of the maximum wavelet coefficient).

After processing module 132 sets the relatively small wavelet coefficients to zero, relatively few wavelet coefficients may remain. In some examples, of the approximately 50 initial wavelet coefficients that may be initially generated to represent the cardiac cycle, only 8-20 of those coefficients may remain. Prior to determining the amount of similarity between the cardiac cycle and the dual-peak template, processing module 132 may perform the simplification procedure on both the cardiac cycle wavelet coefficients and the dual-peak template wavelet coefficients.

Processing module 132 may determine the amount of similarity between the reduced number of cardiac cycle wavelet coefficients and the reduced number of dual-peak wavelet coefficients in a similar manner as processing module 132 compares the time-domain cardiac cycle to the time-domain dual-peak template. For example, processing module 132 may compare the reduced set of coefficients on a coefficient-by-coefficient basis, and determine a matching score based on the comparisons. Processing module 132 may use fewer computational resources during the comparison, relative to a time domain comparison, since there is a reduced number of comparisons to be made relative to a time domain comparison.

FIG. 9 shows a method for determining a morphology of a cardiac cycle by comparing a transform of the cardiac cycle and a transform of the dual-peak template. Prior to the start of the method of FIG. 9, processing module 132 may have acquired a cardiac cycle, characterized the cardiac cycle, and aligned the cardiac cycle to the dual-peak template according to, for example, to blocks (10)-(14) of FIG. 1.

After alignment of the cardiac cycle with the dual-peak template in the time domain (14), processing module 132 may perform a transform (e.g., a Haar wavelet transform) on the cardiac cycle and a transform (e.g., a Haar wavelet transform) on the dual-peak template (500). Although processing module 132 is described as performing a Haar wavelet transform on the cardiac cycle and the dual-peak template, it is contemplated that processing module 132 may perform other types of transforms on the cardiac cycle and the dual-peak template in order to decrease the amount of processing resources used during the matching operation relative to a time-domain matching operation.

Processing module 132 may then perform a simplification of the wavelet coefficients of the cardiac cycle and the dual-peak template by setting the relatively small wavelet coefficients to zero (502). For example, processing module 132 may set wavelet coefficients to zero if the wavelet coefficient is less than a predetermined fractional amount of the largest wavelet coefficient. Processing module 132 may determine a matching score based on a comparison of the simplified cardiac cycle wavelet coefficients and the simplified dual-peak template wavelet coefficients (504).

Processing module 132 may then compare the matching score to a matching threshold in order to determine whether the cardiac cycle matches the dual-peak template morphology or does not match the dual-template morphology in blocks (18)-(22). For example, as illustrated in FIG. 1 and FIG. 9, processing module 132 may determine whether the matching score is greater than a matching threshold (18). If the matching score is greater than the matching threshold, processing module 132 may determine that the cardiac cycle matches the dual-peak template morphology (20). If the matching score is less than the matching threshold, processing module 132 may determine that the cardiac cycle does not match the dual-peak template morphology (22).

Processing module 132 may be configured to perform various digital signal processing operations on the cardiac cycle and the dual-peak template in the time domain prior to alignment of the cardiac cycle and the dual-peak template. The digital signal processing operations described hereinafter include a low-pass filtering operation and a second-order difference operation, although other digital signal processing operations may be implemented by processing module 132 on the cardiac cycle and/or the dual-peak template prior to alignment.

The various digital signal processing operations may provide for a more reliable alignment operation, e.g., an alignment operation that provides for more frequent proper alignments and a reduction in a number of improper alignments. The reliability of an alignment operation may be judged based on the frequency which the alignment operation produces matching scores that are indicative of the actual morphological similarities present between the cardiac cycle and the dual-peak template. In general, an alignment operation may be considered more reliable when the alignment operation tends to align similar morphologies of a cardiac cycle and a dual-peak template, assuming such similar morphologies actually exist between the cardiac cycle and the dual-peak template. It follows then that a more reliable alignment operation may more frequently produce higher matching scores between cardiac cycles and dual-peak templates since similar morphologies may be aligned more frequently than may be the case with less reliable alignment operations. In the scenario where the cardiac cycle and the dual-peak template do not include similar morphologies (i.e., the morphologies are actually not a match), an alignment operation may not generally produce a matching score that indicates similarity, regardless of the reliability of the alignment operation.

FIG. 10 shows a method for time-domain processing of a cardiac cycle and a dual-peak template prior to alignment. Prior to the start of the method of FIG. 10, memory 134 may include one or more cardiac cycles and a dual-peak template. Processing module 132 may retrieve a cardiac cycle and the dual-peak template from memory 134 (600). Processing module 132 may perform a low-pass filtering operation on both the cardiac cycle and the dual-peak template (602). The low-pass filtering operation may include filtering both the cardiac cycle and the dual-peak template using a low pass-filter having a cut-off frequency of approximately 35 Hz, although other frequencies are contemplated. In some examples, processing module 132 may implement an infinite impulse filter (IIR) filter to achieve the 35 Hz low pass filter.

The low-pass filtering operation may eliminate some of the higher frequency content included in the cardiac cycle and the dual-peak template that may otherwise cause peak detection problems. In one example, the cardiac cycle and/or dual-peak template may include high frequency (e.g., >35 Hz) noise, such as sampling noise, or other noise components that may case abrupt spikes or dips in the sampled waveform. Such noise may, in some examples, exaggerate or minimize peaks that are otherwise indicative of cardiac electrical activity. In other examples, such noise may cause peaks to occur where peaks may otherwise not have occurred in the waveforms. In some examples, this noise may cause processing module 132 to identify peaks that may be caused by noise, and are therefore not indicative of cardiac electrical activity. Misidentification of peaks may potentially cause errors in alignment of the cardiac cycle and the dual-peak template and subsequent mis-identification of the morphology of the cardiac cycle.

Elimination of the higher frequency content using low-pass filtering may eliminate components of the cardiac cycle and the dual-peak template that may not be physiologically significant, such as spikes, or other noise. Accordingly, removal of such noise using a low-pass filter operation may increase the reliability of the alignment operation of the present disclosure.

In some examples, processing module 132 may perform a second-order difference operation on the cardiac cycle and/or the dual-peak template (604). The second-order difference operation may function as a high-pass filter to filter out low frequency components of the cardiac cycle and/or the dual-peak template. Low frequency components may include low-frequency drift in the baseline of the cardiac cycle. The second-order difference operation may also make the wavelet transform operation more accurate, since, in some examples, a wavelet transform operation may not normalize wavelet coefficients and may artificially exaggerate low-frequency components.

Although a filtering operation and a second-order difference operation may be performed in series on the cardiac cycle and/or the dual-peak template, in other examples, the difference operation may be performed before the filtering operation. In still other examples, one of the difference operation and the filtering operation may be performed, but not the other. Accordingly, in some examples, the method of FIG. 10 may include block (602) followed by block (604). In other examples, the method of FIG. 10 may include block (602), but not block (604), while in other examples, the method of FIG. 10 may include block (604), but not block (602).

Although a filtering operation and a second-order difference operation are described as being performed on a cardiac cycle and the dual-peak template in the time domain prior to alignment, in some examples, processing module 132 may perform a filtering operation and/or a second-order difference operation on a cardiac cycle and a single-peak template before aligning the cardiac cycle with the single-peak template. These digital signal processing operations on the cardiac cycle and the single-peak template performed prior to alignment may provide for a more reliable alignment operation, e.g., an alignment operation that provides for more frequent proper alignments and a reduction in a number of improper alignments.

Processing module 132 may characterize the cardiac cycle (606) and align the cardiac cycle with the dual-peak template (608) after performing the filtering and second-order difference operations on the cardiac cycle and/or the dual-peak template. Processing module 132 may then perform wavelet transforms on the cardiac cycle and the dual-peak template (610), and, in some examples, processing module 132 may simplify the transformed waveforms, as described above with respect to the method of FIG. 9, blocks (500)-(502). Processing module 132 may then determine an amount of similarity between the cardiac cycle and the dual-peak template based on the remaining wavelet coefficients (612). Processing module 132 may determine whether the amount of similarity is greater than a threshold amount of similarity (18), e.g., based on comparison of a matching score to a matching score threshold. If the matching score is greater than the matching score threshold, processing module 132 may determine that the cardiac cycle matches the dual-peak template morphology (20). If the matching score is less than the matching score threshold, processing module 132 may determine that the cardiac cycle does not match the dual-peak template morphology (22).

In FIGS. 9-10, various processing techniques are performed on the dual-peak template, e.g., a wavelet transform of block (500), a low-pass filtering operation (602), and a second-order difference operation (604). Although these processing techniques are described as performed on the dual-peak template and the cardiac cycle in the same blocks, in other examples, these processing techniques may be performed on the dual-peak template prior to the start of the methods of FIG. 9 and FIG. 10, and the processed dual-peak template may be stored for retrieval and use in these methods.

FIGS. 11-14 illustrate alignments of various cardiac cycles and templates using different alignment techniques. FIGS. 11-14 compare a typical alignment technique to alignment techniques of the present disclosure. As illustrated and described hereinafter, the alignment techniques of the present disclosure may provide more reliable alignment than the typical alignment technique since the alignment technique of the present disclosure tends to better align morphologies of the cardiac cycle and the template when similar morphologies truly exist between the cardiac cycle and the template. FIGS. 11-14 are illustrated in the time domain. The X-axis of each of FIGS. 11-14 indicate sample numbers (e.g. 0-50). The cardiac cycles of FIGS. 11-14 may have been sampled at 256 Hz. The Y-axis of FIGS. 11-14 may indicate analog-to-digital conversion values, i.e., the magnitude of the sampled data for each sample point (e.g., 0 corresponds to 0 mv).

Figure 11A:
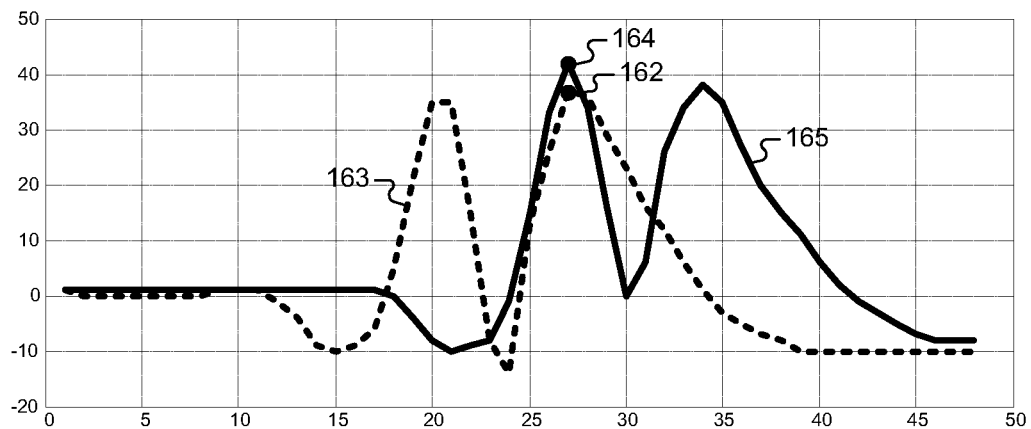
FIGS. 11A-11C show a comparison between a typical alignment procedure and the alignment procedure of the present disclosure.

FIG. 11A illustrates a typical alignment technique in which the largest peak 162 of the cardiac cycle 163 (dotted line) is aligned with the largest peak 164 of the template 165 (solid line). Although the morphology of the cardiac cycle 163 and the template 165 are actually similar, the alignment achieved by the typical alignment technique may not yield an appropriate matching score because the typical alignment technique did not correctly align the similar morphologies of the cardiac cycle 163 and the template 165. For example, the alignment illustrated in FIG. 11A may yield a matching score of 0%.

Figure 11B:
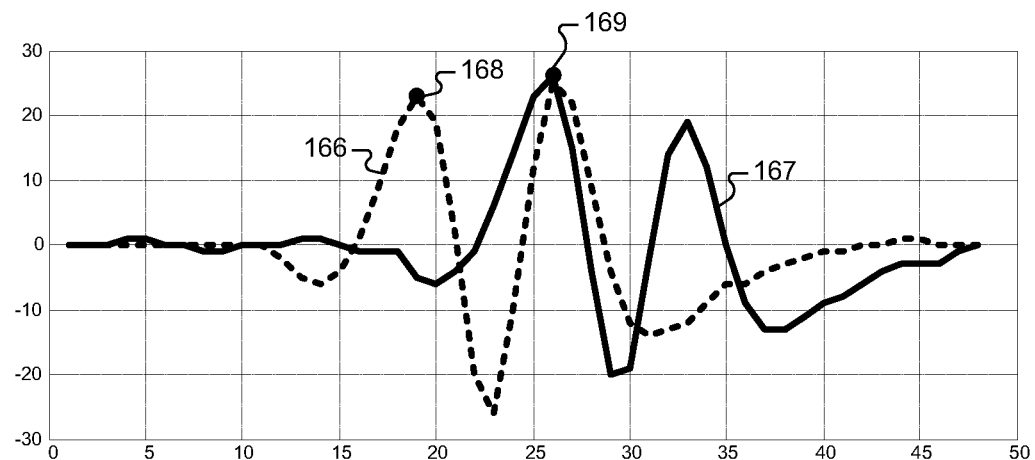

The cardiac cycle 163 and template 165 were processed using a filtering operation (e.g., low-pass 35 Hz filter) and a second-order difference operation to yield cardiac cycle 166 and template 167 of FIG. 11B. Alignment point 168 of cardiac cycle 166 and alignment point 169 of template 167 may have been determined according to the methods of FIGS. 5 and 6. Two positive peaks are clearly ascertainable in the cardiac cycle 166 and the template 167 of FIG. 11B. In FIG. 11B, the smaller peak occurs in the cardiac cycle 166 before the larger peak occurs, while the larger peak occurs in the template 167 before the smaller peak occurs. Accordingly, the peak order of the cardiac cycle 166 and the peak order of the template 167 are opposite, and therefore, the leftmost peaks may be aligned. The alignment points 168, 169 corresponding to the leftmost peaks are illustrated in FIG. 11B.

Figure 11C:
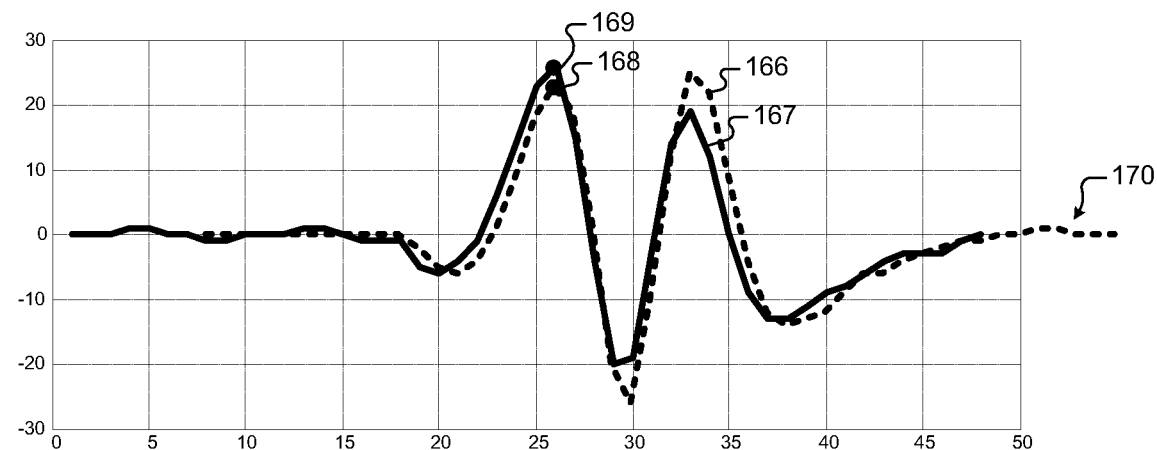

FIG. 11C illustrates the cardiac cycle 166 and the template 167 after shifting of the cardiac cycle 166 to align the alignment points 168, 169, e.g., as described in the method of FIG. 7. Note that a portion 170 of the cardiac cycle 166 has been shifted out of the 50 point window. This portion 170 may not be used when determining the matching score between the cardiac cycle 166 and the template 167. As the portion 170 is shifted out of the window, new values may be added to the left side of the cardiac cycle 166. As aligned in FIG. 11C, the matching score may be approximately 75%, which may indicate a match, assuming a threshold matching score of approximately 70%. Therefore, the alignment procedure of the present disclosure properly aligned the similar morphologies of the acquired cardiac cycle 163 and the template 165 when a typical alignment procedure would not have produced such successful results, i.e., the typical alignment procedure would not have detected a match.

Figure 12A:
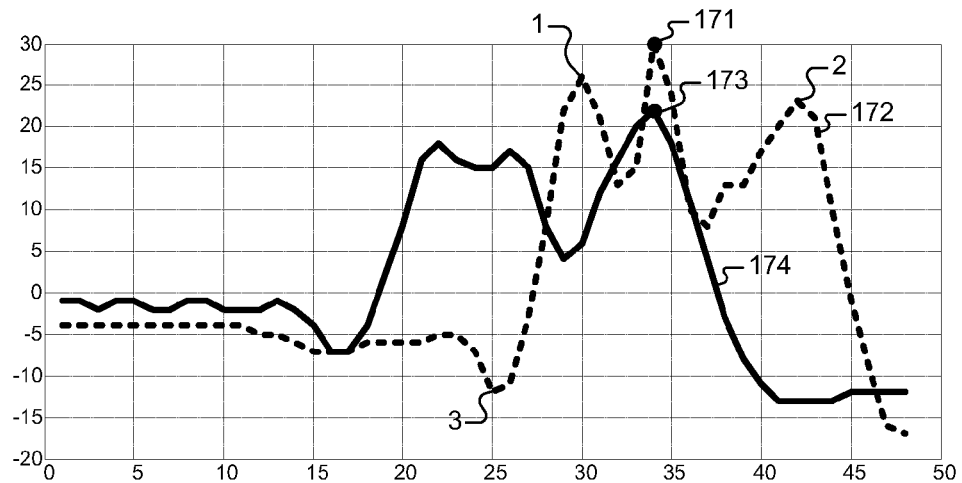
FIGS. 12A-12C show another comparison between a typical alignment procedure and the alignment procedure of the present disclosure.
Figure 12B:
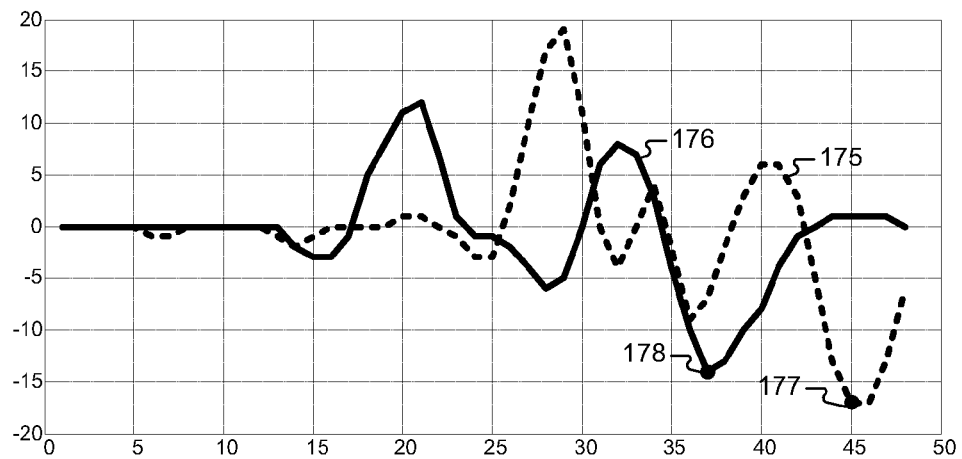
Figure 12C:
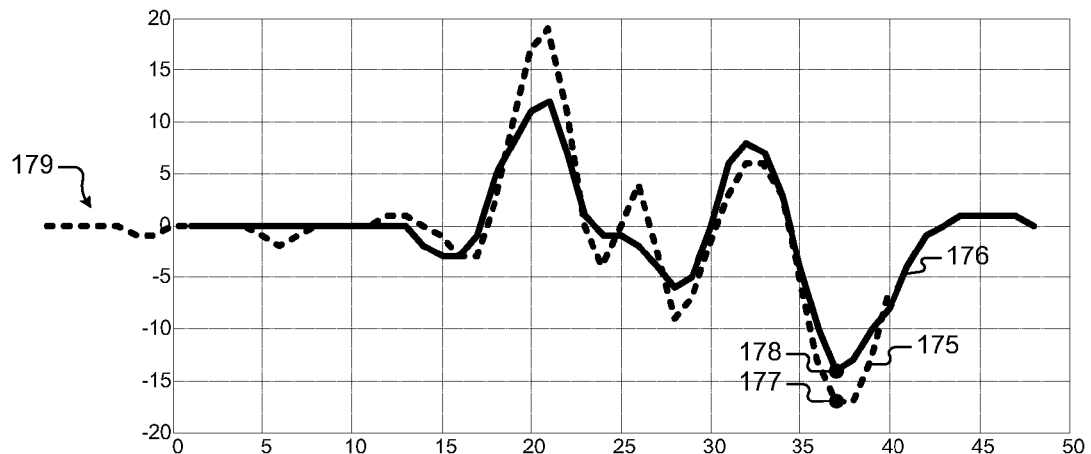

Referring now to FIGS. 12A-12C, another comparison between a typical alignment procedure and the alignment procedure of the present disclosure is illustrated. FIG. 12A illustrates a typical alignment technique in which the largest peak 171 of the cardiac cycle 172 (dotted line) is aligned with the largest peak 173 of the template 174 (solid line). Although the morphology of the cardiac cycle 172 and the template 174 are actually similar, the alignment achieved by the typical alignment technique may not yield an appropriate matching score because the typical alignment technique did not correctly align the similar morphologies of the cardiac cycle 172 and the template 174. For example, the alignment illustrated in FIG. 12A may yield a matching score of 0%.

The cardiac cycle 172 and template 174 were processed using a filtering operation (e.g., 35 Hz low-pass filter) and a second-order difference operation to yield cardiac cycle 175 and template 176 of FIG. 12B. Alignment point 177 (the largest peak) of cardiac cycle 175 and alignment point 178 (the largest peak) of template 176 may have been determined according to the methods of FIGS. 5 and 6. In some examples, according to the method of FIG. 6, the cardiac cycle 175 may have been identified as a single-peak cycle if the second peak of the cardiac cycle 175 having the same polarity as peak 177 was not sufficiently large enough to classify cardiac cycle 175 as a dual-peak cycle. In other examples, even if cardiac cycle 175 was classified as a dual-peak cycle, the largest peaks of the cardiac cycle 175 and the template 176 would be aligned because the peak orders of the cardiac cycle 175 and the template 176 are the same (i.e., smaller peak followed by a larger peak).

FIG. 12C illustrates the cardiac cycle 175 and the template 176 after shifting of the cardiac cycle 175 to align the alignment points 177, 178, e.g., as described in the method of FIG. 7. Note that a portion 179 of the cardiac cycle 175 has been shifted out of the 50 sample window. This portion 179 may not be used when determining the matching score between the cardiac cycle 175 and the template 176. As the portion 179 is shifted out of the window, new values may be added to the right side of the cardiac cycle 175. As aligned in FIG. 12C, the matching score may be approximately 72%, which may indicate a match, assuming a threshold matching score of approximately 70%. Therefore, the alignment procedure of the present disclosure properly aligned the similar morphologies of the acquired cardiac cycle 172 and the template 174 when a typical alignment procedure would not have produced such successful results.

Figure 13A:
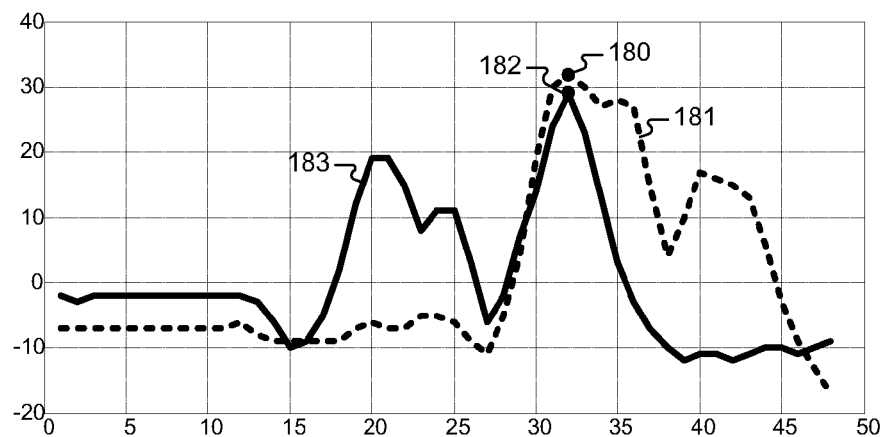
FIGS. 13A-13C show another comparison between a typical alignment procedure and the alignment procedure of the present disclosure.
Figure 13B:
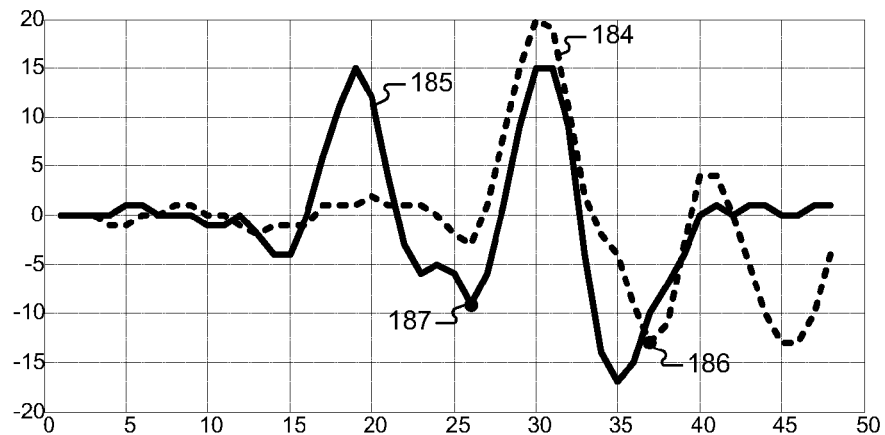
Figure 13C:
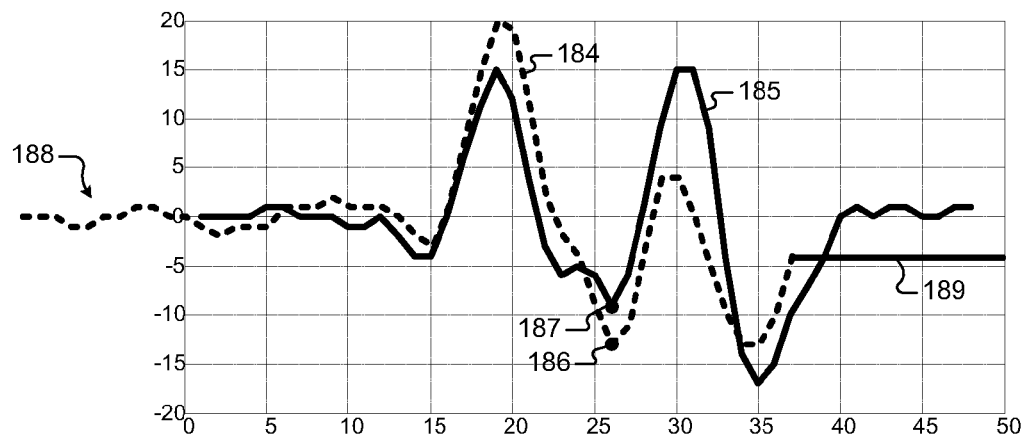

Referring now to FIGS. 13A-13C, another comparison between a typical alignment procedure and the alignment procedure of the present disclosure is illustrated. FIG. 13A illustrates a typical alignment technique in which the highest peak 180 of the cardiac cycle 181 (dotted line) is aligned with the highest peak 182 of the template 183 (solid line). Although the morphology of the cardiac cycle 181 and the template 183 share some morphological similarities, the alignment achieved by the typical alignment technique may not yield an appropriate matching score because the typical alignment technique did not correctly align the similar morphologies of the cardiac cycle 181 and the template 183. For example, a large portion of the cardiac cycle 181 (e.g., sample points 38-45) that includes a peak is aligned over a relatively flat portion of the template 183. The alignment illustrated in FIG. 13A may yield a matching score of 7%.

The cardiac cycle 181 and template 183 were processed using a filtering operation (e.g., a 35 Hz low-pass filter) and a second-order difference operation to yield cardiac cycle 184 and template 185 of FIG. 13B. Alignment point 186 (the larger peak) of cardiac cycle 184 and alignment point 187 (the smaller peak) of template 185 may have been selected according to the methods of FIGS. 5 and 6. Two negative peaks are clearly ascertainable in the cardiac cycle 184 and the template 185 of FIG. 13B. In FIG. 13B, although the negative peaks appear to have similar values, the peak having alignment point 186 may be the larger of the two negative peaks. The smaller peak occurs in the template 185 before the larger peak. Accordingly, the peak order of the cardiac cycle 184 and the peak order of the template 185 are opposite, and therefore, the leftmost peaks may be aligned.

FIG. 13C illustrates the cardiac cycle 184 and the template 185 after shifting of the cardiac cycle 184 to align the alignment points 186, 187, e.g., as described in the method of FIG. 7. Note that a portion 188 of the cardiac cycle 184 has been shifted out of the 50 sample window. This portion 184 may not be used when determining the matching score between the cardiac cycle 184 and the template 185. As the portion 188 is shifted out of the window, new values may be added to the right side of the cardiac cycle 184. Example new values are indicated by the straight solid line portion 189 of the otherwise dotted line indicating the cardiac cycle 184. In this example, the new values may be equal to the original rightmost value of the cardiac cycle 184, e.g., the rightmost value of the cardiac cycle in FIG. 13B. In other examples, as described above, the new values added to the right side of the cardiac cycle 184 may be equal to the baseline value (e.g., 0), instead of the rightmost value of the cardiac cycle. As aligned in FIG. 13C, the matching score may be approximately 32%. The 32% matching score obtained using an alignment procedure of the present disclosure may be more indicative of the actual morphological similarities present between cardiac cycle 181 and template 183 than the matching score of 7% as determined after a typical alignment procedure.

Figure 14A:
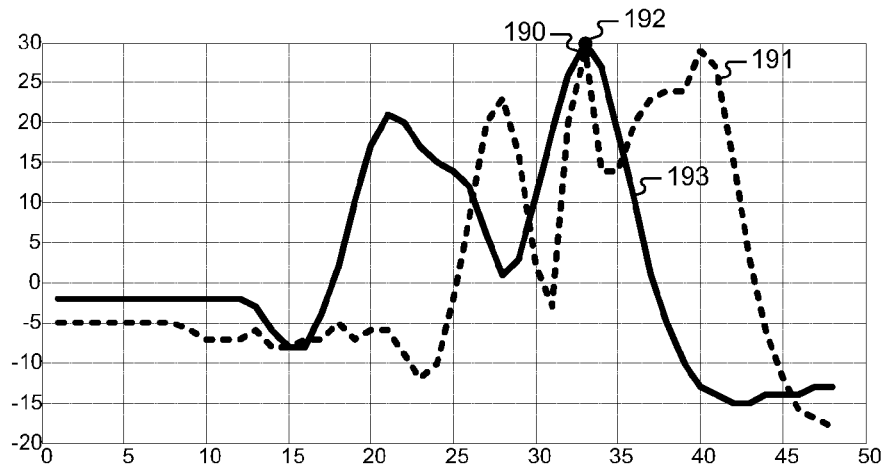
FIGS. 14A-14C show another comparison between a typical alignment procedure and the alignment procedure of the present disclosure.
Figure 14B:
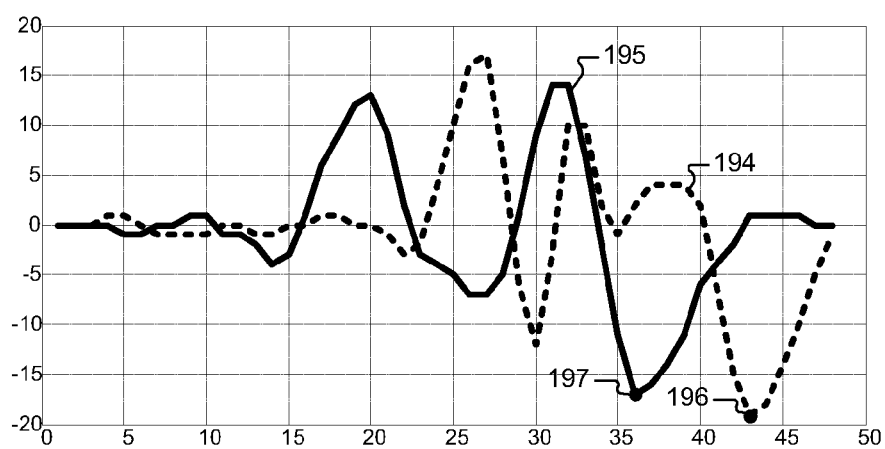
Figure 14C:
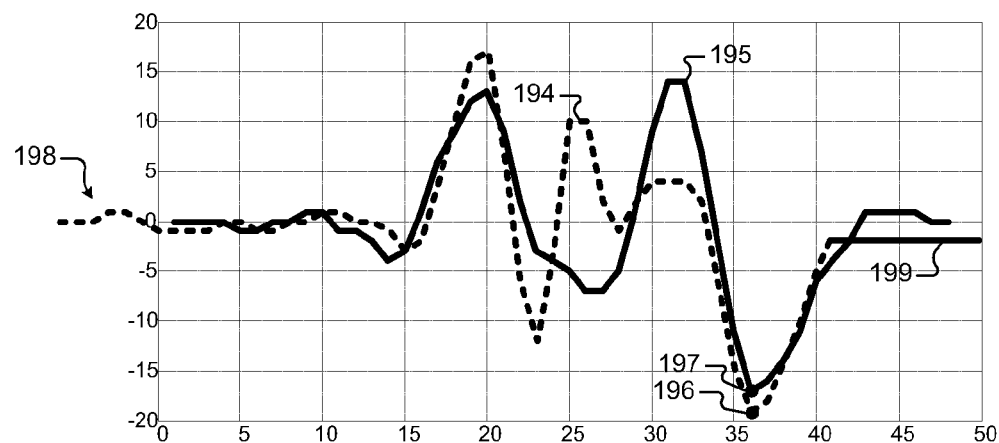
Figure 15:
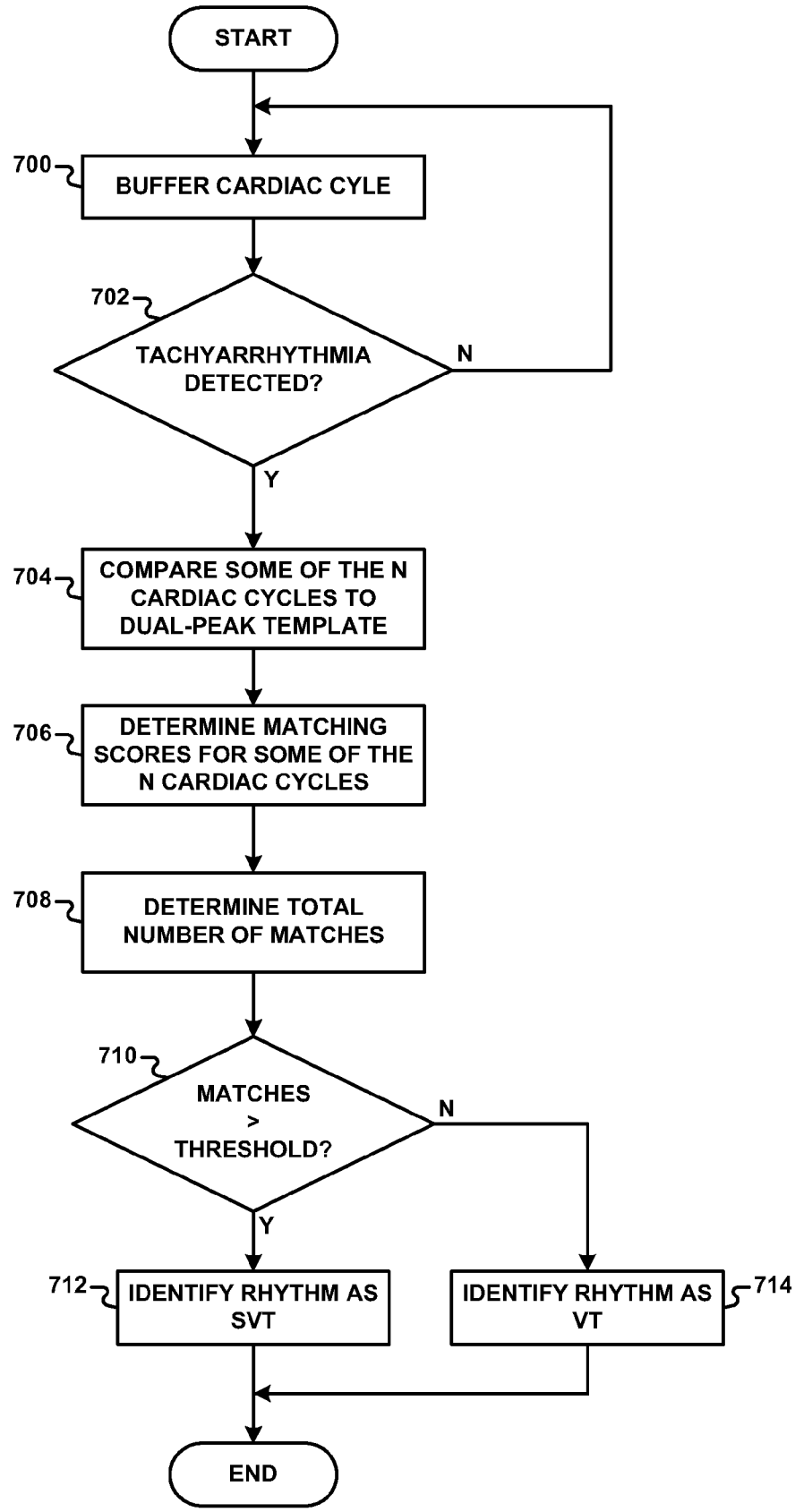
FIG. 15 shows an example method for identifying a rhythm of a plurality of cardiac cycles using a dual-peak template matching procedure.

Referring now to FIGS. 14A-14C, another comparison between a typical alignment procedure and the alignment procedure of the present disclosure is illustrated. FIG. 14A illustrates a typical alignment technique in which the largest peak 190 of the cardiac cycle 191 (dotted line) is aligned with the largest peak 192 of the template 193 (solid line). Although the morphology of the cardiac cycle 191 and the template 193 share some morphological similarities, the alignment achieved by the typical alignment technique may not yield an appropriate matching score because the typical alignment technique did not correctly align the similar morphologies of the cardiac cycle 191 and the template 193. For example, a large portion of the cardiac cycle 191 (e.g., sample points 40-48), that includes a peak, is aligned over a relatively flat portion of the template 193. For example, the alignment illustrated in FIG. 14A may yield a matching score of 0%.

The cardiac cycle 191 and template 193 were processed using a filtering operation (e.g., 35 Hz low-pass filter) and a second-order difference operation to yield cardiac cycle 194 and template 195 of FIG. 14B. Alignment point 196 (the largest peak) of cardiac cycle 194 and alignment point 197 (the largest peak) of template 195 may have been selected according to the methods of FIGS. 5 and 6. In some examples, according to the method of FIG. 6, the cardiac cycle 194 may have been identified as a dual-peak cycle since the cardiac cycle 194 includes 2 prominent negative peaks. The smaller peaks occur before the larger peaks in both the cardiac cycle 194 and the template 195. Accordingly, the peak orders of the cardiac cycle 194 and the template 195 are the same, and the largest peaks of the cardiac cycle 194 and the template 195 may therefore be selected for alignment.

FIG. 14C illustrates the cardiac cycle 194 and the template 195 after shifting of the cardiac cycle 194 to align the alignment points 196, 197, e.g., as described in the method of FIG. 7. Note that a portion 198 of the cardiac cycle 194 has been shifted out of the 50 sample window. This portion 198 may not be used when determining the matching score between the cardiac cycle 194 and the template 195. As the portion 198 is shifted out of the window, new values may be added to the right side of the cardiac cycle 194. Example new values are indicated by the straight solid line portion 199 of the otherwise dotted line indicating the cardiac cycle 194. In this example, the new values may be equal to the original rightmost value of the cardiac cycle 194, e.g., the rightmost value of the cardiac cycle 194 in FIG. 14B. In other examples, as described above, the new values added to the right side of the cardiac cycle 194 may be equal to the baseline value (e.g., 0), instead of the rightmost value of the cardiac cycle 194. As aligned in FIG. 14C, the matching score may be approximately 60%, which may not indicate a match, assuming a threshold matching score of approximately 70%. Even though the alignment techniques of the present disclosure did not yield a matching score that clearly indicates a match, such results may be expected since the cardiac cycle 194 and the template 195 do not include highly similar morphologies, regardless of the alignment techniques used.

In some examples, processing module 132 may analyze a plurality of cardiac cycles using the matching operation described in either FIG. 1 or FIG. 10, for example, in order to identify a rhythm indicated by the plurality of cardiac cycles. For example, processing module 132 may detect a tachyarrhythmia during operation, and when processing module 132 detects a tachyarrhythmia, processing module 132 may perform the matching operation (e.g., of either FIG. 1 or FIG. 10) on a plurality of the cardiac cycles included in the tachyarrhythmia in order to more specifically identify the tachyarrhythmia.

FIG. 15 shows an example method for identifying a rhythm of a plurality of cardiac cycles using a dual-peak template matching procedure. Prior to the start of the method of FIG. 15, processing module 132 may have buffered a plurality of cardiac cycles in memory 134. In the example method of FIG. 15, it may be assumed that processing module 132 buffered N (e.g., 12) cardiac cycles in memory 134, e.g., in a FIFO buffer. It may also be assumed that memory 134 includes a dual-peak template that is indicative of a normal cardiac cycle, e.g., a cardiac cycle having a normal conduction pattern that is free of arrhythmia. Thus, in the example method of FIG. 15, if a cardiac cycle matches well with the dual-peak template, the cardiac cycle may be indicative of a normal conduction pattern, e.g., originating outside of the ventricle.

If the cardiac cycles of the detected tachyarrhythmia match well with the dual-peak template, the tachyarrhythmia may be classified as an SVT, for example, since SVT conduction patterns may not differ from normal conduction patterns in some examples. If the cardiac cycles of the detected tachyarrhythmia do not match well with the template, the tachyarrhythmia may be classified as VT, for example, since VT conduction patterns may differ from normal conduction patterns.

Initially, processing module 132 may buffer a cardiac cycle (700) and then determine whether a tachyarrhythmia is present (702) based on the N buffered cardiac cycles. For example, processing module 132 may detect a tachyarrhythmia using a rate-based detection algorithm, as described above. If processing module 132 does not detect a tachyarrhythmia at block (702), processing module 132 may buffer a new cardiac cycle (700). If processing module 132 detects a tachyarrhythmia at block (702), processing module 132 may compare some or all of the N cardiac cycles included in the tachyarrhythmia to the dual-peak template as described above with respect to either FIG. 1 or FIG. 10, for example, in order to further determine the rhythm (e.g., SVT or VT) indicated by the cardiac cycles (704). Processing module 132 may determine the matching scores for each of the comparisons between a cardiac cycle and the dual-peak template (706) and may determine a total number of matches for all of the comparisons (708).

Processing module 132 may then determine whether the number of matches is greater than a threshold number of matches (710) (e.g., 8 matches out of 12 comparisons). The threshold number of matches may be a user programmable value that may be programmed by a clinician via programmer 130. If processing module 132 determines that the number of matches is greater than the threshold number of matches, processing module 132 may identify the rhythm as an SVT (712) and provide electrical therapy to treat the SVT. If processing module 132 determines that the number of matches is less than the threshold number of matches, processing module 132 may identify the rhythm as VT (714) and provide electrical therapy to treat the VT.

Although the dual-peak template alignment operation is described above as being performed by an implantable medical device (e.g., IMD 106), in some example, an external device may perform the dual-peak template alignment operation. In one example, a computing device external to patient 104 (e.g., programmer 130 or a general purpose computer) may retrieve one or more cardiac cycles from IMD 106 and determine the morphology of the one or more cardiac cycles using the dual-peak alignment operation. Although retrieving EGM data for a plurality of cardiac cycles is described above as being performed by IMD 106 (e.g., electrical sensing module 138), in other examples, cardiac cycle data may be retrieved using external electrocardiogram (ECG) electrodes attached to patient 104. For example, an ECG device may retrieve cardiac cycles via the ECG electrodes attached to patient 104. The ECG device, or other external computing device, may then determine the morphology of the cardiac cycles using the dual-peak alignment operation based on the externally sampled cardiac cycles according to the techniques of the present disclosure.

In still other examples, sampled cardiac cycles (e.g., sampled either internally or externally) may be stored and/or processed on a remote computing device, e.g., a computing device located remotely from patient 104. For example, the cardiac cycle data may be transferred via a network to a remote datastore and/or computing device. The network may include a wide area network (WAN) and/or the Internet, for example. The network may also include a shorter range network, such as a local area network (LAN). Such cardiac cycle data stored in the datastore may be retrieved at a later time by a computing device (e.g., via the network) for analysis.

Various examples have been described. These and other examples are within the scope of the following claims.

The invention claimed is:

1. A method comprising:
storing an electrogram (EGM) template in a memory, the EGM template including first and second alignment points at first and second peaks of the EGM template, respectively;
identifying first and second peaks of a cardiac cycle EGM acquired by a medical device;
selecting one of the first and second peaks of the cardiac cycle EGM to align with one of the first and second alignment points based on an order in which the first and second peaks of the cardiac cycle EGM occur;
aligning the selected one of the first and second peaks with one of the first and second alignment points; and
determining an amount of similarity between the cardiac cycle EGM and the EGM template after alignment;
performing a second-order difference operation on the cardiac cycle EGM and the EGM template before identifying the first and second peaks of the cardiac cycle EGM and selecting one of the first and second peaks of the cardiac cycle EGM.

2. The method of claim 1, wherein the EGM template includes a normal cardiac electrical conduction pattern.

3. The method of claim 2, further comprising determining that the cardiac cycle EGM includes a normal cardiac electrical conduction pattern when the amount of similarity is greater than a threshold amount of similarity.

4. The method of claim 1, wherein identifying the first and second peaks of the cardiac cycle EGM comprises:
identifying the largest peak of the cardiac cycle EGM having the same polarity as the first and second peaks of the EGM template;
identifying the second largest peak of the cardiac cycle EGM having the same polarity as the largest peak of the cardiac cycle EGM; and
identifying the largest peak and the second largest peak of the cardiac cycle EGM as the first and second peaks of the cardiac cycle EGM, respectively.

5. The method of claim 4, wherein the order in which the first and second peaks of the cardiac cycle EGM occur defines which of the largest peak and the second largest peak of the cardiac cycle EGM occurs first.

6. The method of claim 4, wherein the largest peak and the second largest peak have negative polarities.

7. The method of claim 1, wherein aligning the selected one of the first and second peaks with one of the first and second alignment points comprises:
overlaying the cardiac cycle EGM onto the EGM template; and
shifting the cardiac cycle EGM until the selected one of the first and second peaks is aligned with the one of the first and second alignment points.

8. The method of claim 1, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, and wherein the first and second peaks of the EGM template and the first and second peaks of the cardiac cycle EGM have the same polarity.

9. The method of claim 1, further comprising aligning the selected one of the first and second peaks with one of the first and second alignment points based on an order in which the first and second alignment points occur.

10. The method of claim 9, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, and wherein the first and second peaks of the EGM template and the first and second peaks of the cardiac cycle EGM have the same polarity.

11. A method comprising:
storing an electrogram (EGM) template in a memory, the EGM template including first and second alignment points at first and second peaks of the EGM template, respectively;

identifying first and second peaks of a cardiac cycle EGM acquired by a medical device;
selecting one of the first and second peaks of the cardiac cycle EGM to align with one of the first and second alignment points based on an order in which the first and second peaks of the cardiac cycle EGM occur;
aligning the selected one of the first and second peaks with one of the first and second alignment points;
determining an amount of similarity between the cardiac cycle EGM and the EGM template after alignment;
aligning the selected one of the first and second peaks with one of the first and second alignment points based on an order in which the first and second alignment points occur, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, and wherein the first and second peaks of the EGM template and the first and second peaks of the cardiac cycle EGM have the same polarity; and
aligning the first alignment point and the first peak of the cardiac cycle EGM when the order, by magnitude, of the first and second peaks of the cardiac cycle EGM is the same as the order, by magnitude, of the first and second peaks of the EGM template.

12. A method comprising:
storing an electrogram (EGM) template in a memory, the EGM template including first and second alignment points at first and second peaks of the EGM template, respectively;
identifying first and second peaks of a cardiac cycle EGM acquired by a medical device;
selecting one of the first and second peaks of the cardiac cycle EGM to align with one of the first and second alignment points based on an order in which the first and second peaks of the cardiac cycle EGM occur;
aligning the selected one of the first and second peaks with one of the first and second alignment points;
determining an amount of similarity between the cardiac cycle EGM and the EGM template after alignment;
aligning the selected one of the first and second peaks with one of the first and second alignment points based on an order in which the first and second alignment points occur, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, and wherein the first and second peaks of the EGM template and the first and second peaks of the cardiac cycle EGM have the same polarity; and
aligning the leftmost alignment point of the first and second alignment points and the leftmost peaks of the first and second peaks of the cardiac cycle EGM when the order, by magnitude, of the first and second peaks of the cardiac cycle EGM is different than the order, by magnitude, of the first and second peaks of the EGM template.

13. A method comprising:
storing an electrogram (EGM) template in a memory, the EGM template including first and second alignment points at first and second peaks of the EGM template, respectively;
identifying first and second peaks of a cardiac cycle EGM acquired by a medical device;
selecting one of the first and second peaks of the cardiac cycle EGM to align with one of the first and second alignment points based on an order in which the first and second peaks of the cardiac cycle EGM occur;
aligning the selected one of the first and second peaks with one of the first and second alignment points;
determining an amount of similarity between the cardiac cycle EGM and the EGM template after alignment; and
applying a low-pass filter to the cardiac cycle EGM and the EGM template before identifying the first and second peaks of the cardiac cycle EGM and selecting one of the first and second peaks of the cardiac cycle EGM.

14. A method comprising:
storing an electrogram (EGM) template in a memory, the EGM template including first and second alignment points at first and second peaks of the EGM template, respectively;
identifying first and second peaks of a cardiac cycle EGM acquired by a medical device:
selecting one of the first and second peaks of the cardiac cycle EGM to align with one of the first and second alignment points based on an order in which the first and second peaks of the cardiac cycle EGM occur;
aligning the selected one of the first and second peaks with one of the first and second alignment points;
determining an amount of similarity between the cardiac cycle EGM and the EGM template after alignment; and
performing a wavelet transform on the cardiac cycle EGM and the EGM template after aligning the selected one of the first and second peaks with one of the first and second alignment points, wherein determining the amount of similarity between the cardiac cycle EGM and the EGM template comprises determining the amount of similarity between the transformed cardiac cycle EGM and the transformed EGM template.

15. The method of claim 1, further comprising delivering electrical therapy to a heart of a patient based on the amount of similarity between the cardiac cycle EGM and the EGM template.

16. A device comprising:
a memory; and
a processing module configured to:
store an electrogram (EGM) template in the memory, the EGM template including first and second alignment points at first and second peaks of the EGM template, respectively;
acquire a cardiac cycle EGM;
identify first and second peaks of the cardiac cycle EGM;
select one of the first and second peaks of the cardiac cycle EGM to align with one of the first and second alignment points based on an order in which the first and second peaks of the cardiac cycle EGM occur;
align the selected one of the first and second peaks with one of the first and second alignment points;
determine an amount of similarity between the cardiac cycle EGM and the EGM template after alignment; and
perform a second-order difference operation on the cardiac cycle EGM and the EGM template before identifying the first and second peaks of the cardiac cycle EGM and selecting one of the first and second peaks of the cardiac cycle EGM.

17. The device of claim 16, wherein, to identify the first and second peaks of the cardiac cycle EGM, the processing module configured to:
  identify the largest peak of the cardiac cycle EGM having the same polarity as the first and second peaks of the EGM template;
  identify the second largest peak of the cardiac cycle EGM having the same polarity as the largest peak of the cardiac cycle EGM; and
  identify the largest peak and the second largest peak of the cardiac cycle EGM as the first and second peaks of the cardiac cycle EGM, respectively,
  wherein the order in which the first and second peaks of the cardiac cycle EGM occur defines which of the largest peak and the second largest peak of the cardiac cycle EGM occurs first.

18. The device of claim 16, wherein the processing module is configured to align the selected one of the first and second peaks with one of the first and second alignment points based on an order in which the first and second alignment points occur.

19. The device of claim 18, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, and wherein the first and second peaks of the EGM template and the first and second peaks of the cardiac cycle EGM have the same polarity.

20. A device comprising:
  a memory; and
  a processing module configured to:
    store an electrogram (EGM) template in the memory, the EGM template including first and second alignment points at first and second peaks of the EGM template, respectively;
    acquire a cardiac cycle EGM;
    identify first and second peaks of the cardiac cycle EGM;
    select one of the first and second peaks of the cardiac cycle EGM to align with one of the first and second alignment points based on an order in which the first and second peaks of the cardiac cycle EGM occur;
    align the selected one of the first and second peaks with one of the first and second alignment points;
    determine an amount of similarity between the cardiac cycle EGM and the EGM template after alignment, wherein the processing module is configured to align the selected one of the first and second peaks with one of the first and second alignment points based on an order in which the first and second alignment points occur, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, wherein the first and second peaks of the EGM template and the first and second peaks of the cardiac cycle EGM have the same polarity, and wherein the processing module is configured to align the first alignment point and the first peak of the cardiac cycle EGM when the order, by magnitude, of the first and second peaks of the cardiac cycle EGM is the same as the order, by magnitude, of the first and second peaks of the EGM template.

21. A device comprising:
  a memory; and
  a processing module configured to:
    store an electrogram (EGM) template in the memory, the EGM template including first and second alignment points at first and second peaks of the EGM template, respectively;
    acquire a cardiac cycle EGM;
    identify first and second peaks of the cardiac cycle EGM;
    select one of the first and second peaks of the cardiac cycle EGM to align with one of the first and second alignment points based on an order in which the first and second peaks of the cardiac cycle EGM occur;
    align the selected one of the first and second peaks with one of the first and second alignment points;
    determine an amount of similarity between the cardiac cycle EGM and the EGM template after alignment, wherein the processing module is configure to align the selected one of the first and second peaks with one of the first and second alignment points based on an order in which the first and second alignment points occur, wherein the first and second peaks of the EGM template include the largest and the second largest peaks of the EGM template, respectively, wherein the first and second peaks of the cardiac cycle EGM include the largest and the second largest peaks of the cardiac cycle EGM, respectively, wherein the first and second peaks of the EGM template and the first and second peaks of the cardiac cycle EGM have the same polarity, and wherein the processing module is configured to align the leftmost alignment point of the first and second alignment points and the leftmost peak of the first and second peaks of the cardiac cycle EGM when the order, by magnitude, of the first and second peaks of the cardiac cycle EGM is different than the order, by magnitude, of the first and second peaks of the EGM template.

* * * * *

UNITED STATES PATENT AND TRADEMARK OFFICE
CERTIFICATE OF CORRECTION

PATENT NO. : 8,521,268 B2
APPLICATION NO. : 13/104743
DATED : August 27, 2013
INVENTOR(S) : Xusheng Zhang and Jeffrey M. Gillberg Page 1 of 1

It is certified that error appears in the above-identified patent and that said Letters Patent is hereby corrected as shown below:

In the claims,

Col. 30, line 4, delete "alignment points; and determining" and insert in place thereof -- alignment points; determining --;

Col. 30, line 6, delete "after alignment; performing" and insert in place thereof -- after alignment; and performing --;

Col. 34, line 31, delete "module is configure to align" and insert in place thereof -- module is configured to align --.

Signed and Sealed this
Twenty-first Day of April, 2015

Michelle K. Lee
*Director of the United States Patent and Trademark Office*